United States Patent
Lee et al.

(10) Patent No.: US 12,350,404 B2
(45) Date of Patent: Jul. 8, 2025

(54) 3D-POROUS HYBRID ANTI-INFLAMMATORY NANOSCAFFOLD FOR DRUG DELIVERY AND TISSUE ENGINEERING

(71) Applicant: Rutgers, The State University of New Jersey, New Brunswick, NJ (US)

(72) Inventors: Ki-Bum Lee, Monmouth Junction, NJ (US); Letao Yang, Edison, NJ (US); Brian Conley, West Windsor, NJ (US)

(73) Assignee: RUTGERS, THE STATE UNIVERSITY OF NEW JERSEY, New Brunswick, NJ (US)

(*) Notice: Subject to any disclaimer, the term of this patent is extended or adjusted under 35 U.S.C. 154(b) by 0 days.

(21) Appl. No.: 16/874,313

(22) Filed: May 14, 2020

(65) Prior Publication Data
US 2021/0015975 A1     Jan. 21, 2021

Related U.S. Application Data

(63) Continuation-in-part of application No. PCT/US2018/061301, filed on Nov. 15, 2018.
(Continued)

(51) Int. Cl.
| | | |
|---|---|---|
| A61L 27/54 | (2006.01) | |
| A61K 9/00 | (2006.01) | |
| A61K 33/32 | (2006.01) | |
| A61K 38/00 | (2006.01) | |
| A61K 47/36 | (2006.01) | |
| A61L 31/14 | (2006.01) | |
| B82Y 5/00 | (2011.01) | |
| C12N 5/0793 | (2010.01) | |
| B82Y 40/00 | (2011.01) | |

(52) U.S. Cl.
CPC ............ *A61L 27/54* (2013.01); *A61K 9/0024* (2013.01); *A61K 33/32* (2013.01); *A61K 38/00* (2013.01); *A61K 47/36* (2013.01); *A61L 31/148* (2013.01); *C12N 5/0619* (2013.01); *B82Y 5/00* (2013.01); *B82Y 40/00* (2013.01)

(58) Field of Classification Search
CPC .... A61K 33/32; A61L 2400/12; A61L 31/148
See application file for complete search history.

(56) References Cited

U.S. PATENT DOCUMENTS

| 10,100,332 B2 | 10/2018 | Lee et al. |
| 2005/0176647 A1 | 8/2005 | Sugiyama et al. |

(Continued)

FOREIGN PATENT DOCUMENTS

| WO | 2013/059831 A1 | 4/2013 |

OTHER PUBLICATIONS

Yang et al. "A biodegradable hybrid organic nanoscaffold for advanced stem cell therapy", Nature Communications, Aug. 8, 2018, vol. 9, pp. 1-14. (Year: 2018).*
(Continued)

*Primary Examiner* — Carlos A Azpuru
*Assistant Examiner* — Casey S Hagopian
(74) *Attorney, Agent, or Firm* — FOX ROTHSCHILD LLP

(57) ABSTRACT

The invention relates to biodegradable nanoscaffolds, e.g. low dimension manganese oxide ($MnO_2$)-based nanoscaffolds containing ECM proteins and/or cationic polymers, and methods of use and manufacture thereof.

9 Claims, 6 Drawing Sheets

Specification includes a Sequence Listing.

Related U.S. Application Data

(60) Provisional application No. 62/586,468, filed on Nov. 15, 2017.

(56) References Cited

U.S. PATENT DOCUMENTS

| | | | |
|---|---|---|---|
| 2009/0047272 | A1 | 2/2009 | Appelbaum et al. |
| 2010/0316702 | A1 | 12/2010 | Briggs et al. |
| 2012/0294903 | A1* | 11/2012 | Guo .................. C08L 5/08 422/600 |
| 2016/0302928 | A1 | 10/2016 | Day et al. |
| 2018/0117218 | A1* | 5/2018 | Han .................. A61K 9/0024 |
| 2020/0390806 | A1* | 12/2020 | Sharma .................. A61K 9/14 |

OTHER PUBLICATIONS

Corning Matrigel Matrix. Accessed online on Apr. 26, 2022 at https://www.corning.com. (Year: 2022).*

Zhang et al., MnO2-Based Nanoplatform Serves as Drug Vehicle and MRI Contrast Agent for Cancer Theranostics, ACS Applied Materials & Interfaces Mar. 2017 9 (13), 11337-11344. (Year: 2017).*

Chinaglia et al. Biodegradation rate of biodegradable plastics at molecular level, Polymer Degradation and Stability vol. 147, Jan. 2018, pp. 237-244. (Year: 2018).*

Zheng et al. Biodegradable metals, Materials Science and Engineering R 77 (2014) pp. 1-34. (Year: 2014).*

Yang et al. "Fabrication of nano-structured porous PLLA scaffold intended for nerve tissue regeneration", Biomaterials 25 (2004) pp. 1891-1900. (Year: 2004).*

Chimene et al. "Two-Dimensional Nanomaterials for Biomedical Applications: Emerging Trends and Future Prospects" Adv. Mater. 2015, 27, 7261-7284. (Year: 2015).*

Yang et al. "A biodegradable hybrid inorganic nanoscaffold for advanced stem cell therapy", Nature, Aug. 2018, 9:3147, pp. 1-14. (Year: 2018).*

Shah, et al: "Guiding Stem Cell Differentiation into Oligodendrocytes using Graphene-Nanofiber Hybrid Scaffolds", Advanced Materials, Mar. 26, 2014, 26.22, pp. 1-8.

Chen, et al: "Break-up of Two-Dimensional MnO2 Nanosheets Promotes Ultrasensitive pH-Triggered Theranostics of Cancer", Advanced Materials, Aug. 22, 2014, 26.41, pp. 1-8.

Li, et al: "Biodegradable MnO2 Nanosheet-Mediated Signal Amplification in Living Cells Enables Sensitive Detection of Down-Regulated Intracellular MicroRNA", ACS Applied Materials & Interfaces, Jan. 26, 2017, 9,7, pp. 1-21.

Yang, et al: "A Biodegradable Hybrid Inorganic Nanoscaffold for Advanced Stem Cell Therapy", Nature Communications, Aug. 8, 2018, vol. 9, pp. 1-14.

Dey, et al: "Characterizing Molecular Adsorption on Biodegradable MnO Nanoscaffolds", The Journal of Physical Chemistry, Nov. 27, 2018, pp. 1-34.

Han, et al: "MnO2 Nanorods Intercalating Graphene Oxide/ Polyaniline Ternary Composites for Robust High-Performance Supercapacitors", Scientific Reports, Apr. 28, 2014, 4 : 4824, DOI: 10.1038/srep04824, pp. 1-7.

Liu, et al: "Electrostatic-Interaction-Assisted Construction of 3D Networks of Manganese Dioxide Nanosheets for Flexible High-Performance Solid-State Asymmetric Supercapacitors", ACS Nano, 2017, 11, pp. 7879-7888, DOI: 10.1021/acsnano.7b02344.

Wang, et al: "Novel Multi-Drug Delivery Hydrogel Using Scar-Homing Liposomes Improves Spinal Cord Injury Repair", Theranostics, 2018; 8(16): pp. 4429-4446. doi: 10.7150/thno.26717.

Johnson, et al: "Electrospun Fiber for Drug Delivery after Spinal Cord Injury and the Effects of Drug Incorporation on Fiber Properties", Cells Tissues Organs, 2015, 16;202: pp. 116-135, DOI: 10.1159/000446621.

Lan, et al: "Implantable Porous Gelatin Microspheres Sustained Release of bFGF and Improved its Neuroprotective Effect on Rats After Spinal Cord Injury", PLOS One, Mar. 14, 2017, pp. 1-16 [retrieved from internet: <<https://doi.org/10.1371/journal.pone. 0173814>>].

Agbasi-Porter, et al., Transcription Inhibition Using Oligonucleotide-Modified Gold Nanoparticles, Bioconjugate Chemistry, vol. 17, No. 5, Sep. 1, 2006, pp. 1178-1183.

Liu, et al., Delivery of Intact Transcription Factor by Using Self-Assembled Supramolecular Nanoparticles, Angewandte Chemie International Edition, vol. 50, No. 13, Mar. 21, 2011, pp. 3058-3062.

Patel, et al., NanoScript: A Nanoparticle-Based Artificial Transcription Factor for Effective Gene Regulation, ACS Nano, vol. 8, No. 9, Aug. 18, 2014, pp. 8959-8967.

Xiao, et al., A Cell-Permeable Synthetic Transcription Factor Mimic, Angewandte Chemie International Edition, vol. 46, No. 16, Apr. 13, 2007, pp. 2865-2868.

Timmers et al: "Nuclear and Nucleolar Localization of Saccharomyces Cerevisiae Ribosomal Proteins S22 and S25", FEBS Letters, 1999, vol. 452, pp. 335-340.

Ragin, et al: "Cellular Import Mediated by Nuclear Localization Signal Peptide Sequences", Chemistry & Biology, Aug. 2002, vol. 8, pp. 943-948.

International Search Report and Written Opinion issued Feb. 24, 2015 in PCT International Application No. PCT/US14/52569 (11 pages).

Extended European Search Report issued Jan. 31, 2017 in European Patent Application No. 14837321.0 (9 pages).

Non-Final Office Action issued Apr. 21, 2017 in U.S. Appl. No. 14/913,804 (11 pages).

Final Office Action issued Sep. 8, 2017 in U.S. Appl. No. 14/913,804 (11 pages).

Notice of Allowance issued Oct. 4, 2021 in U.S. Appl. No. 16/437,898 (12 pages).

* cited by examiner

FIG. 1b *Tunable Biodegradation (MnO₂)*

*Efficient Drug Loading and Sustained Release*

*FRET/MRI-based Monitoring of Drug Release*

*Nanomaterial-enabled Advanced Stem Cell Therapy*

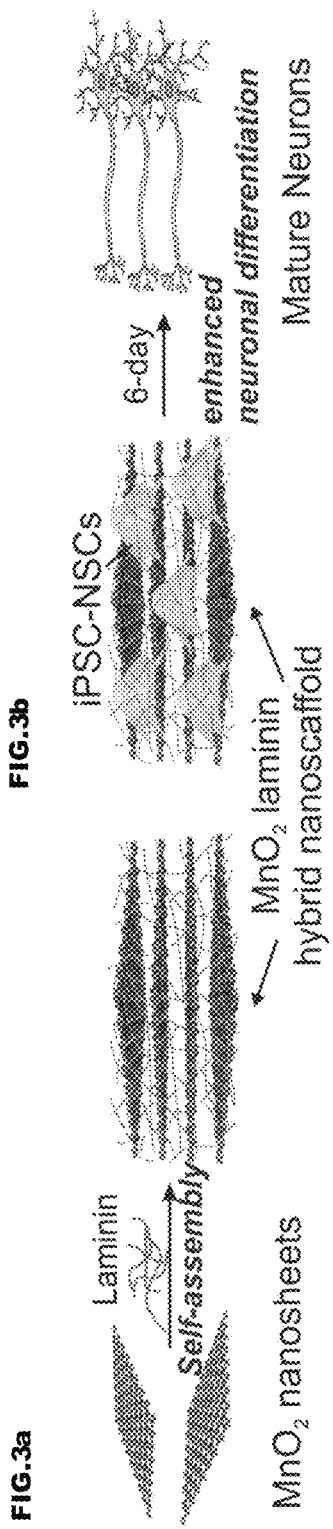

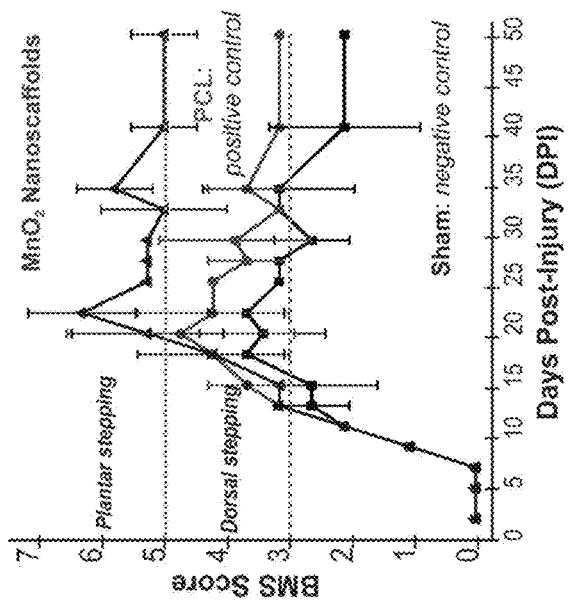
Fig. 4a
Fig. 4b
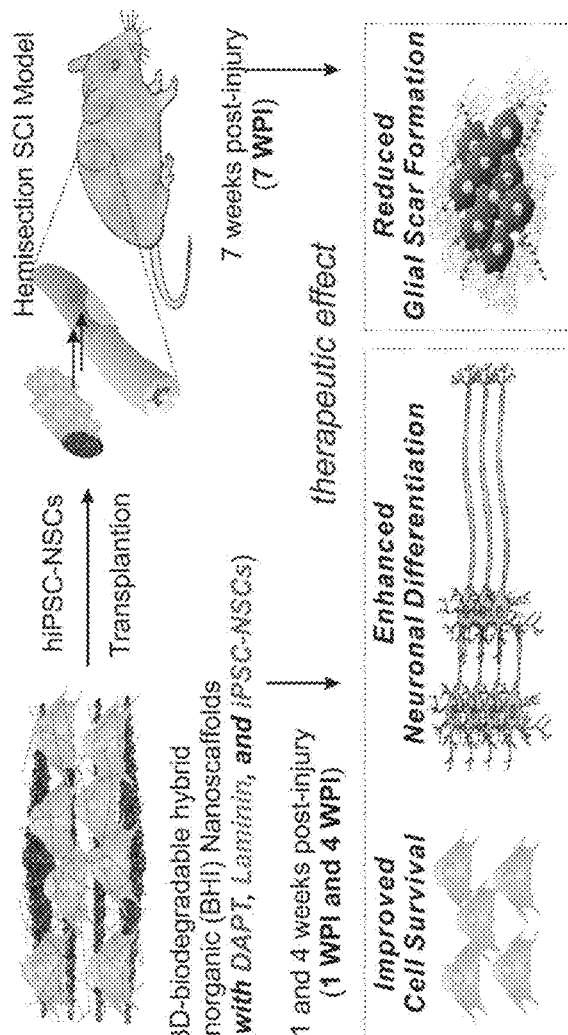
Fig. 4c

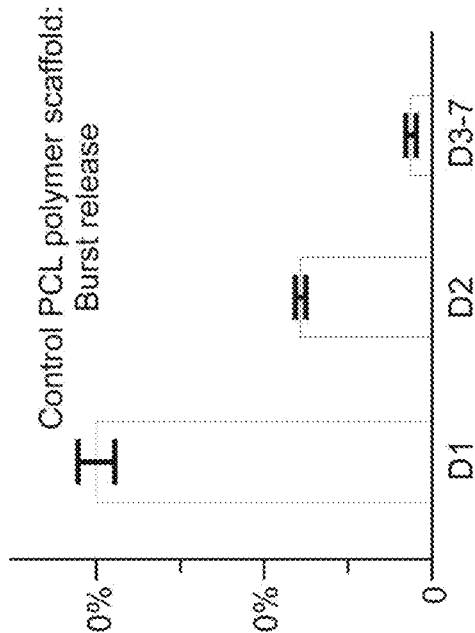
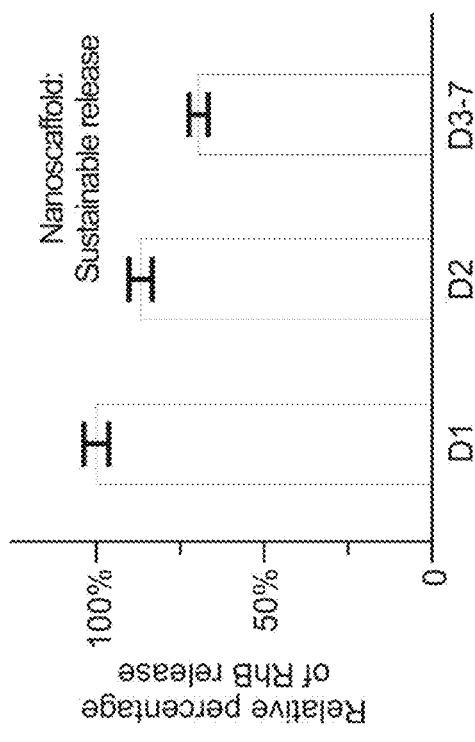
Fig. 5a
Fig. 5b

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
ccgcatcttc ttttgcgtcg    20

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
gcccaatacg accaaatccg t                                              21

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
ggtgtccgag taccagcagt                                                20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ttcgtacatc tcgccctctt                                                20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
aggaagattg agtcgctgga                                                20

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
aacctcctcc tcgtgggatc t                                              21

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
tggtgcaatg gagcgagtat t                                              21

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
gggacttcag agtggagctg                                                20

<210> SEQ ID NO 9

-continued

```
<211> LENGTH: 20
<212> TYPE: DNA
<213> ORGANISM: Artificial Sequence
<220> FEATURE:
<223> OTHER INFORMATION: primer

<400> SEQUENCE: 9
atgactctac ccacggcaag                                              20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
cagtgaacct cctctgaccg                                              20

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
actttatctt cggtcagagt g                                            21

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
ctcacgacat ccaggactga                                              20

<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13
gagagagatt cgcactcagt a                                            21

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
tgaggtctgc aaacttggac                                              20
```

3D-POROUS HYBRID ANTI-INFLAMMATORY NANOSCAFFOLD FOR DRUG DELIVERY AND TISSUE ENGINEERING

CLAIM OF PRIORITY

This application is a continuation-in-part of International Application No. PCT/US18/61301, filed Nov. 15, 2018, which claims the benefit of U.S. Provisional Application No. 62/586,468, all of which applications are incorporated herein by reference.

STATEMENT REGARDING FEDERAL FUNDING

This invention was made with government support under grant numbers NS085569, OD006462 awarded by the National Institutes of Health (NIH) and grant numbers 1236508, 1429062 awarded by the National Science Foundation (NSF). The U.S. government has certain rights in the invention.

FIELD OF THE INVENTION

The field of the invention is to low dimension manganese oxide ($MnO_2$)-based biodegradable hybrid inorganic support structures for delivery of cells and therapeutic agents, and methods of use and manufacture thereof.

BACKGROUND

Developing reliable therapeutic methods to treat central nervous system (CNS) diseases (e.g. Alzheimer's and Parkinson's diseases), degeneration in the aging brain, and CNS injuries (e.g. spinal cord injury (SCI) and traumatic brain injuries), is a current a major challenge, due to the complex and dynamic cellular microenvironment during the disease progression. Current therapeutic approaches aim to restore neural signaling, reduce neuro-inflammation, and prevent subsequent damage to the injured area, using stem cell therapies. However, there are many current limitations with using stem cell therapies. Due to the inflammatory nature of the injured regions, most of the cells perish soon after transplantation. Additionally, the extracellular matrix (ECM) of the damaged areas is not conducive to stem cell survival and differentiation. Accordingly, there is a need for better approaches to increase the survival rate of transplanted stem cells, and to better control stem cell fate in vivo, which can lead to the recovery of the damaged neural functions and the repair of neuronal connections in a more effective manner.

One possibility is the use of nanoscaffolding material. There are currently four main types of scaffolds in the art. These include hydrogels, polymeric scaffolds, micropatterned surface microplates, and nanofiber based scaffolds. Most of these scaffolds, however, once used for transplantation purposes, will burst release therapeutic drugs, which negatively influences the survival or differentiation of the cells transplanted. These negative effects on cellular fates and disease treatment are further deteriorated by the lack of cellular binding moieties on most of current scaffold technologies. As such, there is an urgent need for improved nanoscaffolding that mimics the natural environment for these therapeutic purposes, for example, for stem cell therapy.

SUMMARY OF THE INVENTION

The present disclosure relates to biodegradable nanoscaffolding material that possesses a number of surprising therapeutic benefits and uses, as well as methods of making the nanoscaffolding material.

Accordingly, in a first aspect of the invention, there is provided a biodegradable scaffolding material comprising a plurality of at least one of zero-dimension, one-dimension or two-dimension manganese dioxide support structures, and at least one of a plurality of extracellular matrix proteins or a plurality of cationic polymers, wherein the zero-dimension, one-dimension or two-dimension manganese dioxide support structures define a structure comprising a plurality of interstices; wherein the plurality of extracellular matrix proteins or plurality of cationic polymers are disposed around and between the zero-dimension, one-dimension or two-dimension manganese dioxide support structures and through the zero-dimension, one-dimension or two-dimension manganese dioxide support structure interstices; and wherein the extracellular matrix proteins or cationic polymers have a binding affinity with the zero-dimension, one-dimension or two-dimension manganese dioxide support structures, and together form at least one 3-dimensional nanoscaffold.

According to one embodiment of the invention, the zero-dimension, one-dimension or two-dimension manganese dioxide support structures comprise at least one of, 0-dimensional nanoparticles, 1-dimensional manganese dioxide nanotubes, 1-dimensional manganese dioxide nanorods, or 2-dimensional manganese dioxide nanosheets.

According to a different embodiment of the invention, the extracellular matrix proteins comprise at least one of collagen, elastin, laminin, fibronectin, gelatin, a reconstituted basement membrane extracted from Engelbreth-Holm-Swarm mouse tumor (e.g., MATRIGEL®), entactin, proteoglycans, or basement membrane protein. According to yet another embodiment of the invention, the extracellular matrix proteins comprise laminin. According to a further embodiment of the invention, the cationic polymers comprise at least one of extracellular matrix polysaccharides, or non-polysaccharides. According to another embodiment, the non-polysaccharides comprise at least one of polylysine, polyethyleneimine, polyhistidine peptide, polyarginine peptide, H2AFX protein, PARP1 protein, RPS6 protein, a natural low molecular weight tannin polymer, such as TANFLOC™, polyphosphazenes, or a synthetic high molecular weight polyacrylamide polymer, such as FLOPAM™ or ZETAG™. According to a different embodiment, the extracellular matrix polysaccharides comprise at least one of hyaluronic acid, alginate, chitosan, or combinations thereof. According to another embodiment, the biodegradable scaffolding material further comprises at least one therapeutic agent. According a further embodiment, the therapeutic agent comprises at least one of a protein, antibody, nucleic acid, biologic drug, peptide, small molecule, biologic drug, ligand, cytokine, chemotherapeutic agent, antipyretis, analgesis, anesthetis, antibiotic, antiseptic, hormone, stimulant, depressant, statin, beta blocker, anticoagulant, antiviral, anti-fungal, anti-inflammatory, growth factor, vaccine, diagnostic composition, psychiatric medication, or psychoactive compound. According to yet another embodiment of the invention, the biodegradable scaffolding material further comprises at least cell disposed in the nanoscaffold. According to a different embodiment, the at least one cell comprises a stem cell. According to still another embodiment, the stem cells comprise neural stem cells.

In a second aspect of the invention, there is provided a method of treating a disease or disorder in a subject, comprising surgically implanting or injecting the biodegradable scaffolding material of the first aspect of the invention into said subject. According to one embodiment of the invention, the rate of delivery of the therapeutic agent is controlled by tuning the rate of degradation of the zero-dimension, one-dimension or two-dimension manganese dioxide support structures. In another embodiment of the invention, the rate of degradation of the zero-dimension, one-dimension or two-dimension manganese dioxide support structures is tuned by controlling at least one of, the porosity of the scaffolding material, the thickness of the scaffolding material, the aspect ratio of the scaffolding material, extracellular matrix protein concentration, or cellular density. In still another embodiment, the rate at which the biodegradable scaffolding material is degraded in vivo can be measured by detecting the rate of release of Mn 2 ions from the biodegradable scaffolding material.

In a third aspect of the invention, there is provided a method of making the biodegradable scaffolding material, comprising the steps of: providing a first solution containing a plurality of at least one of zero-dimension, one-dimension or two-dimension manganese dioxide support structures; and mixing the first solution with a second solution containing at least one of a plurality of extracellular matrix proteins or a plurality of cationic polymers, to form a resultant mixture containing the biodegradable scaffolding material. In one embodiment, the method further comprises the step of applying a vacuum filtration method to the resultant mixture to isolate the biodegradable scaffolding material. In another embodiment of the invention, the method further comprises the step of centrifuging the resultant mixture prior to applying the vacuum filtration method. According to a different embodiment of the invention, the zero-dimension, one-dimension or two-dimension manganese dioxide support structures comprise at least one of, 0-dimensional nanoparticles, 1-dimensional manganese dioxide nanotubes, 1-dimensional manganese dioxide nanorods, or 2-dimensional manganese dioxide nanosheets In another embodiment, the method further comprises the step of adding at least one therapeutic agent to the first solution prior to mixing the first solution with the second solution. In yet another embodiment of the invention, the therapeutic agent comprises at least one of a protein, antibody, nucleic acid, biologic drug, peptide, small molecule, biologic drug, ligand, cytokine, chemotherapeutic agent, antipyretis, analgesis, anesthetist, antibiotic, antiseptic, hormone, stimulant, depressant, statin, beta-blocker, anticoagulant, antiviral, anti-fungal, anti-inflammatory, growth factor, vaccine, diagnostic composition, psychiatric medication, or psychoactive compound. In still a further embodiment of the invention, the method further comprises the step of adding at least one cell to the first solution prior to mixing the first solution with the second solution. In a different embodiment of the invention, the cell comprises a stem cell. In yet another embodiment of the invention, at least one of the first and second solutions is a buffer solution, and the molar ratio of the extracellular matrix proteins to the zero-dimension, one-dimension or two-dimension manganese dioxide support structures is greater than 1:10.

In a fourth aspect of the invention, there is provided a method of making the biodegradable scaffolding material according to the first aspect of the invention, comprising the steps of: (a) providing a support structure solution containing a plurality of at least one of zero-dimension, one-dimension or two-dimension manganese dioxide support structures; (b) adding at least one cell to the support structure solution; and (c) adding droplets of a solution of the cationic polymers to the support structure solution, wherein the solution of the extracellular matrix cationic polymers has a polymer concentration of greater than 30 mg/ml. In one embodiment, the method further includes the step of adding at least one therapeutic agent to the solution.

BRIEF DESCRIPTION OF THE DRAWINGS

FIGS. 1A, 1B and 1C represent a schematic diagram of enhanced stem cell differentiation and drug delivery using biodegradable $MnO_2$ hybrid nanoscaffolds. FIG. 1A illustrates the key scaffold compositions include one-dimension and two-dimension $MnO_2$ nanostructures and the ECM proteins or cationic polymers. Therapeutic components that can be included in the scaffold include but are not limited to cells and chemotherapeutic drugs. Two dimensional $MnO_2$ nanosheets and one dimensional $MnO_2$ nanotubes or nanorods were used as examples for describing the low dimension $MnO_2$ nanostructures. The exemplary drug shown in the illustration is a Notch inhibitor. The interactions between the chemotherapeutic drug and the one-dimension and two-dimension $MnO_2$ can be studied to predict drug release profiles by computational approaches. FIG. 1B summarizes the unique advantages of $MnO_2$ hybrid nanoscaffolds. FIG. 1C shows a representative scanning electron microscope (SEM) image of the $MnO_2$ hybrid nanoscaffolds.

FIG. 2A illustrates controllable redox biodegradation of $MnO_2$ hybrid nanoscaffolds was demonstrated through cyclic voltammetry. Successful degradation of nanoscaffolds were confirmed by the disappearance of yellow color from nanoscaffold triggered by electrical stimuli. FIG. 2B illustrates degradation of nanoscaffold by commonly existent bioreductants (e.g. vitamin C), indicated by the disappearance of manganese elements from the substrate after degradation through Electron Dispersive X-ray (EDX) analysis (Mn peak: 6.8 eV).

FIGS. 3A and 3B represent 3D $MnO_2$ hybrid nanoscaffolds self-assembled from ECM proteins for versatile stem cell therapy. FIGS. 3A and 3B represent a schematic diagram illustrating the mechanism for the self-assembly of extracellular matrix (ECM) protein (laminin) and 2-D $MnO_2$ nanosheets through a non-covalent crosslinking mechanism. Synthesized $MnO_2$ laminin hybrid nanoscaffolds, and Induced Pluripotent Stem Cell-Derived Neural Stem Cells (iPSC-NSCs) cultured on $MnO_2$-laminin hybrid nanoscaffolds successfully differentiated into functional neurons after 6 days (FIG. 3B).

FIGS. 4A, 4B and 4C represent advanced stem cell therapy for enhanced treatment of spinal cord injury (SCI). FIG. 4A represents a schematic diagram showing the enhanced functional recovery in a murine hemisection SCI model through the transplantation of iPSC-NSC-seeded $MnO_2$ laminin hybrid nanoscaffold and the proposed mechanisms related to the functional recovery. FIG. 4B represents that the Basso Mouse Scale for Locomotion (BMS) score throughout 7-week post-transplantation supports an obviously improved therapeutic potential of stem cells transplanted by the nanoscaffold compared to conventional polymer scaffold and sham group. FIG. 4C represents that the BMS score throughout 7-week post-transplantation supports an improved therapeutic potential of stem cells transplanted by the nanoscaffold, compared to conventional polymer scaffold and sham group.

FIGS. 5A and 5B represent that compared to polycaprolactone (PCL) scaffold, nanoscaffold has a more sustainable release profile through the one-week's processes. Rhodamine B (RhB) releasing was indicated by the brightness of monocolored images (top) and summarized in relative percentage compared to amount of released at Day 1. Scale bars: 200 μm. A movie showing the bioreductant triggered scaffold degradation and drug release. Error bars are the standard error of the mean (n=5).

FIG. 6A represents a degradation profile of different scaffolds obtained from measuring time dependent manganese concentrations in the solution using Inductively Coupled Plasma Mass Spectrometry (ICP-MS). FIG. 6B: represents a summary of full degradation time of scaffolds based on the complete disappearance of scaffold color. $MnO_2$ laminin nanoscaffold was used for all the conditions and regular iPSC-NSC differentiation media was used for maintaining cell viabilities with regular daily media change.

DETAILED DESCRIPTION OF THE INVENTION

Figure 1A:
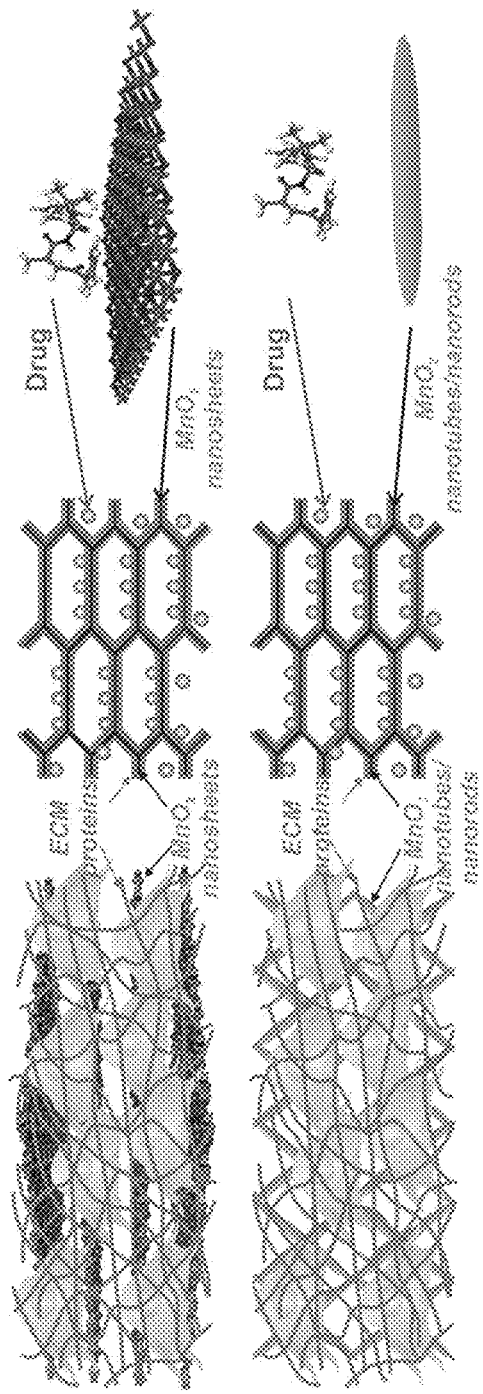

The present disclosure relates to biodegradable hybrid inorganic nanoscaffolds, e.g. biodegradable nanoscaffolds containing low dimension manganese dioxide support structures and at least one of extracellular matrix (ECM) macromolecules or cationic polymers.

There are a number of advantages to the nanoscaffolds of the present disclosure. In addition to being biodegradable, the rate of biodegradation is tunable. The ability to control biodegradability by tuning scaffold properties instead of relying solely on in vivo redox conditions is advantageous because in vivo redox environments may be difficult to control. Another advantage is that the nanoscaffolds can promote stem cell differentiation. Additionally, the nanoscaffolds can be used for the delivery of one or more therapeutic agents. Yet another advantage is that the release of therapeutic agents from the nanoscaffold can be monitored by standard imaging techniques known in the art. Accordingly, the nanoscaffolds of the present disclosure present a number of advantages compared to nanoscaffolds currently in the art, such as graphene-based nanoscaffolds, or synthetic polyurethanes, hydrogels, and the like. The nanoscaffolds of the present disclosure thus have a potential for use in many applications, such as tissue engineering, drug delivery, and stem cell therapy. In particular, with regard to stem cell therapy, applications can include treatment of SCI and other nervous system injuries/disorders (e.g. central nervous system (CNS) and peripheral nervous system (PNS) injuries/disorders), treatment of orthopaedic injuries/disorders (e.g. bone and cartilage), dental, cardiac disease, and/or muscular injuries/disorders, amongst others.

The biodegradable scaffolding material of the invention contains a plurality of low dimension manganese dioxide support structures, and either a plurality of extracellular matrix (ECM) macromolecules or cationic polymers, or both. In one embodiment, the plurality of extracellular matrix macromolecules may be at least one of extracellular matrix proteins (ECM proteins) or extracellular matrix proteoglycans (ECM proteoglycans). In another embodiment, the plurality of cationic polymers may be at least one of extracellular matrix polysaccharides (ECM polysaccharides) or non-polysaccharides. In a different embodiment, the biodegradable scaffolding material contains a plurality of extracellular matrix proteins and a plurality of cationic polymers. The "low dimension" structures may be 0-dimensional, 1-dimensional (ID), 2-dimensional (2D), or any combination thereof. The low dimension manganese dioxide support structures define a structure containing a plurality of interstices.

As noted above, the biodegradable scaffolding material may include only 0D, only 1D, or only 2D manganese dioxide support structures, or any combination thereof. In one embodiment of the invention, plurality of low dimension manganese dioxide support structures includes 2-dimensional nanosheets. In a preferred embodiment of the invention, the nanosheets are 2D $MnO_2$ nanosheets. However, other 2-dimensional metal oxide compositions may be suitable for use in the present invention. Generally, suitable metal oxides include transition metals with a +4 oxidation state bound to two oxygen atoms. Other 2D metal oxides beyond 2D $MnO_2$ that may be suitable for use in the present invention include, for example, vanadium (IV) dioxide ($VO_2$), for example as disclosed in Chem. Commun., 2013, 49, 3943-3945; cobalt (IV) peroxide ($CoO_2$) for example as disclosed in J. Power Sources, 227, 101-105; and nickel (IV) peroxide ($NiO_2$), for example as disclosed in Langmuir, 2014, 30 (47), 14343-14351; each reference hereby incorporated by reference in their entireties. Within the 2D $MnO_2$ nanosheets are a plurality of interstices. The plurality of extracellular matrix proteins and/or the plurality of cationic polymers surround the nanosheets, and also infiltrate the nanosheet interstices, such that they are disposed on all sides of the nanosheets, and also pass through the nanosheets by way of the nanosheet interstices. The extracellular matrix proteins and/or the cationic polymers have a binding affinity with the nanosheets, which causes the nanosheets to self-assemble themselves in such a way as to create a three-dimensional nanoscaffold.

In another embodiment of the invention, the plurality of low dimension manganese dioxide support structures includes 1-dimensional nanotubes and/or nanorods. In a preferred embodiment of the invention, the nanotubes or nanorods are ID $MnO_2$ nanotubes or nanorods. However, other 1-dimensional metal oxide compositions may be suitable for use in the present invention. Generally, suitable metal oxides include the same as those listed herein-above for the nanosheets. The extracellular matrix proteins and/or the cationic polymers have a binding affinity with the 1D nanotubes and nanorods, which causes the nanotubes or nanorods to self-assemble themselves into a lattice, in such a way as to create a three-dimensional nanoscaffold. Between the 1D nanotubes and nanorods in the lattice are a plurality of interstices. The plurality of extracellular matrix proteins and/or the plurality of cationic polymers surround the 1D nanotubes and nanorods in the lattice, and also infiltrate the lattice interstices, such that they are disposed on all sides of the 1D nanotubes and nanorods, and also pass through the lattice interstices.

In a further embodiment, the plurality of low dimension manganese dioxide support structures include 0-dimensional nanoparticles. Generally, suitable metal oxides include the same as those listed herein-above for the nanosheets. The extracellular matrix proteins and/or the cationic polymers have a binding affinity with the 0D nanoparticles, which causes the nanoparticles to self-assemble themselves into a lattice, in such a way as to create a three-dimensional nanoscaffold. Between the 0D nanoparticles in the lattice are a plurality of interstices. The plurality of extracellular matrix proteins and/or the plurality of cationic polymers surround the 0D nanoparticles in the lattice, and also infiltrate the lattice interstices, such that they are disposed on all sides of the 0D nanoparticles, and also pass through the lattice interstices.

Figure 1C:
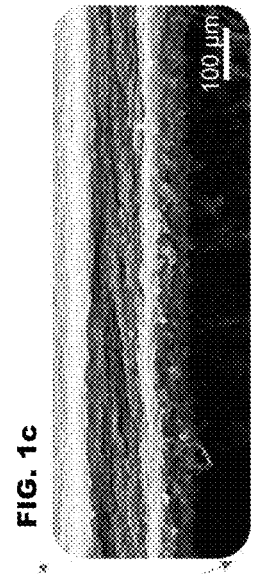

There is no limit to the number of low dimension manganese dioxide support structures that may be used in a nanoscaffold of the invention, as long as the support structures remain on the nano level. The support structures may be situated in any arrangement, relative to one another. They may be arranged substantially parallel to one another, in a way that they are substantially planar, in a random arrangement, or in any combination of the foregoing. The method by which the nanoscaffold is synthesized may influence the way the support structures arrange themselves. For example, when 2D manganese dioxide nanosheets are mixed with ECM protein, the nanosheets may tend to arrange themselves in a random manner; meanwhile, when vacuum filtration is performed on the 2-D $MnO_2$ nanosheets, they may tend to arrange themselves in a substantially parallel manner. In one embodiment of the invention, the 2D manganese dioxide support structures are arranged such that they are substantially planar. In another embodiment of the invention, the 2D manganese dioxide support structures may be disposed substantially parallel to one another, with a network of ECM proteins and/or cationic polymers dispersed throughout the nanoscaffold; for example, see FIG. 3A, which illustrates 2-D $MnO_2$ nanosheets as "stacked" parallel to one another, with a network of ECM proteins networked throughout the biodegradable nanoscaffolding material, and passing through the nanosheet interstices, thereby forming the 3-dimensional nanoscaffolding. In another embodiment of the invention, the 1D manganese dioxide support structures are arranged such that they are substantially planar and/or parallel to one another. In another embodiment of the invention, the ID manganese dioxide support structures may be randomly arranged, with a network of ECM proteins and/or cationic polymers dispersed throughout the nanoscaffold; for example, see FIG. 1, which illustrates 1D $MnO_2$ nanotubes and nanorods randomly arranged, with a network of ECM proteins networked throughout the biodegradable nanoscaffolding material, and passing through the nanotube or nanorod interstices, thereby forming the 3-dimensional nanoscaffolding.

As noted above, the extracellular matrix proteins and/or the cationic polymers have a binding affinity with the low dimension manganese dioxide support structures. The specific mechanism of this binding affinity is not fully known. One theory is that the ECM proteins may interact (i.e. associate with) the low dimension manganese dioxide support structures through intramolecular forces, such as electrostatic interactions and metal-interactions. These type of interactions typically comprise interactions with amine and aromatic functional groups (e.g. through phenylalanine, tyrosine, tryptophan, asparagine, glutamine, lysine, arginine, or histidine amine groups and aromatic sidechains on ECM proteins) and the oxygen and manganese atoms respectively. It is surmised that the amine groups may interact with oxygen via electrostatic interactions, while the π-systems of the aromatic groups may interact with the Mn in the nanoscaffolds. Other potential interactions could include, for example, but not necessarily, ionic bonding, hydrogen bonding, Van der Waals forces, dipole-dipole interactions, dipole-induced forces, London dispersion forces, aromatic ring interactions, hydrophobic interactions, and combinations thereof.

Suitable ECM proteins may include, but are not limited to, any one of laminin, collagen, elastin, fibronectin, gelatin, a reconstituted basement membrane extracted from Engelbreth-Holm-Swarm mouse tumor (e.g., MATRIGEL®), entactin, proteoglycans and basement membrane proteins. In a preferred embodiment, the ECM protein is laminin. Laminins, which form a major component of the basal lamina, are generally high-molecular weight (e.g. ~400 to ~900 kDa) proteins, typically glycoproteins. They influence cellular differentiation, migration, and adhesion. They are generally heterotrimeric proteins that contain an α-chain, a β-chain, and a γ-chain, found in five, four, and three genetic variants, respectively, and are named according to their chain composition. Suitable laminins may include, but are not limited to, any of the following: laminin-111, laminin-211, laminin-121, laminin-221, laminin-332, laminin-3A32, laminin-3B32, laminin-311, laminin-3A11, laminin-321, laminin-3A21, laminin-411, laminin-421, laminin-511, laminin-521, laminin-213, laminin-413, laminin-522, laminin-523, and combinations thereof. Collagens represent the main structural protein in the extracellular space in the various connective tissues in animal bodies and are the most abundant protein in mammals, making up about 25% to about 35% of the total protein content. The most common types of collagen are Type I (found in skin, tendon, vascular ligature, organs, and bone), Type II (found in cartilage), Type III (found in reticular fibers), Type IV (forms the basal lamina), and Type V (found in cell surfaces, hair, and the placenta). Collagens useful for the invention include, for example Type I, Type II, Type III, Type IV, Type V, Type VI, Type VII, Type VIII, Type IX, Type X, Type XI, Type XII, Type XIII, Type XIV, Type XV, Type XVI, Type XVII, Type XVIII, Type XIX, Type XX, Type XXI, Type XXII, Type XXIII, Type XXIV, Type XXV, Type XXVI, Type XXVII, Type XXVIII collagens, and combinations thereof. Suitable proteoglycans include those proteoglycans that make up the extracellular matrix of tissue. Exemplary proteoglycans include, for example, at least one of chondroitin sulfate, heparan sulfate and keratan sulfate, and combinations thereof. Basement membrane proteins include those proteins that make up the extracellular matrix of tissue that separates the epithelium, mesothelium, and endothelium from the underlying connective tissue. Exemplary basement membrane proteins include for example, at least one of fibrillin-1, fibrillin-2, fibrillin-3, fibrillin-4, integrins, dystroglycans, and combinations thereof.

In addition to, or instead of ECM proteins, the biodegradable nanoscaffolds may include cationic polymers. The cationic polymers may have a positive value, during a Zeta potential measurement, under the PH of 7.4, in an aqueous solution. In one embodiment, the cationic polymers may be ECM polysaccharides, which may be natural or synthetic polysaccharide compositions of matter, such as for example, hyaluronic acid, alginate, chitosan, and combinations thereof. In another embodiment, the cationic polymers may be non-polysaccharides, which may be natural or synthetic. Any suitable non-ploysaccharide may be used. Suitable synthetic non-polysaccharide cationic polymers include, for example, a natural low molecular weight tannin polymer, such as TANFLOC™, polyphosphazenes, a synthetic high molecular weight polyacrylamide polymer, such as FLOPAM™ or ZETAG™, and polyethylenimine. Suitable cationic natural polymers include, for example, polylysine, polyhistidine peptide, polyarginine peptide, H2AFX protein, PARP1 protein and RPS6 protein.

In one embodiment of the present invention, the biodegradable nanoscaffolds of the present invention may include one or more therapeutic agents. In this embodiment, one or more of the therapeutic agents may be trapped, or embedded in the nanoscaffold. The therapeutic agents may bind to, or associate with the nanoscaffold. This association may or may not be through interactions similar to that of the ECM proteins with the manganese dioxide in the nanoscaffolding. The therapeutic agents may include, but are not limited to, any therapeutic agents that contain amine and/or aromatic functional groups/side chains. Such compositions are known to one of ordinary skill in the art. For example, therapeutic agents may include, but are not limited to, any of peptides, proteins, antibodies, nucleic acids, biologic drugs, small molecules, cytokines, ligands, and combinations thereof. Other potential therapeutic agents may include, purely by way of example, chemotherapeutic agents, antipyretics, analgesics/anesthetics, antibiotics, antiseptics, hormones, stimulants, depressants, statins, beta blockers, anticoagulants, antivirals, anti-fungals, anti-inflammatory growth factors, vaccines, diagnostic compositions, psychiatric medications/psychoactive compounds, and any related compositions.

In another embodiment of the invention, the biodegradable nanoscaffolds of the present invention may further include cells that may be disposed in and on the nanoscaffold. In one embodiment, these cells may be stem cells, such as for example, any of embryonic stem(ES) cells, adult stem cells, induced pluripotent stem (iPS) cells, induced somatic stem cells (iSC) and combinations thereof. More specifically, the stem cells can include hematopoietic stem cells (HSCs), mammary stem cells, intestinal stem cells, mesenchymal stem cells (MSCs), endothelial stem cells, neural stem cells (NSC), olfactory adult stem cells, neural crest stem cells, testicular cells, adipose-derived stem cells (ADSCs), and combinations thereof. In an exemplary embodiment, the stem cells may be neural stem cells (NSCs), e.g. for treatment of spinal cord injury (SCI). The stem cells may undergo differentiation while embedded in the scaffolding material. This process may be, but is not necessarily, directed by the presence of specific ECM proteins. For example, nanoscaffolds containing laminin may promote differentiation of neural cells, which are useful for treatment of spinal cord injury (SCI), as illustrated by the Examples. Those containing fibronectin may promote myogenesis (differentiation of muscle cells) and osteogenesis (differentiation of bone cells). Meanwhile, nanoscaffolds containing aginate may promote neurogenesis (differentiation of neural cells). One of skill in the art will recognize that there are a number of ECM proteins, including but not limited to those disclosed herein, which may result in different stem cell differentiation. The nanoscaffolds may thus be used for autologous grafting, e.g. autologous nerve grafting, allografting, or even xenografting.

Figure 6B:
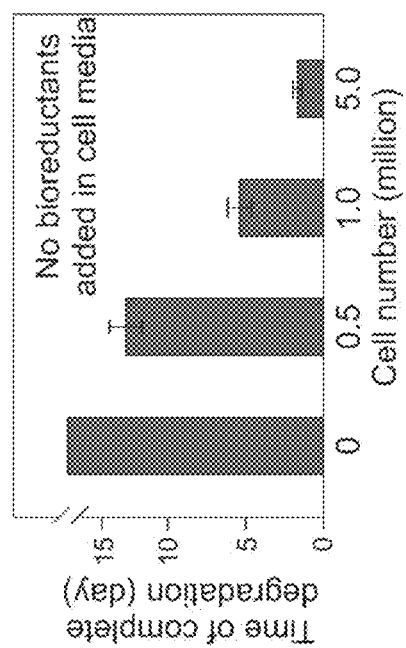
FIGS. 6A and 6B represent tuning biodegradability of $MnO_2$ nanoscaffolds by modulating scaffold structure and varying cell densities.
Figure 6A:
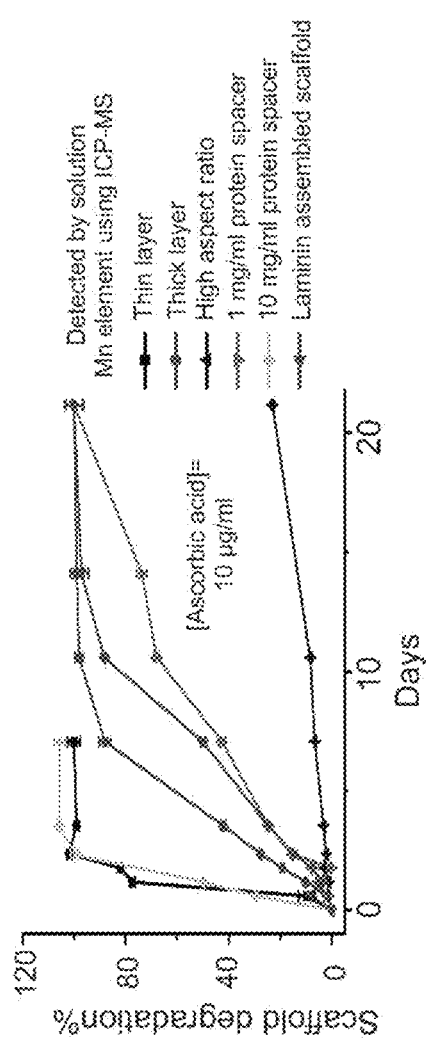

Low dimension manganese dioxide support structures degrade in the presence of cell metabolism outputs, such as ascorbic acid, according to a classic reduction-oxidation mechanism. In vivo, the main mechanism for controlling the rate of degradation of the low dimension manganese dioxide support structures is the porosity of the scaffold. The rate of degradation of the low dimension manganese dioxide support structures may also be controlled by other means, such as for example, controlling the thickness of the $MnO_2$ layers in the nanoscaffold, the aspect ratio (height to surface area ratio) of the nanoscaffold, the extracellular matrix protein concentration, the concentration of reductants, modifying interlayer binding species (for example, ions and proteins, e.g. but not limited to spacer proteins, including bovine serum albumin) or the cellular density. Briefly, as shown in the Examples and in FIG. 6, reducing the thickness of the nanoscaffold by 5 times can increase the degradation speed by about 3 times; increasing the aspect ratio slows down the degradation speed by over 10 times; and increasing the protein concentrations utilized to assemble nanosheets lead to a significant increase around 7 times. In one embodiment of the invention, the rate of biodegradation of the nanoscaffolds is tunable, by any of these means, preferably by changing the porosity of the scaffolding material. Likewise, the rate at which the therapeutic agent or cells are released is also tunable. This is due to the fact that, the rate at which the therapeutic agent or cells are released from the biodegradable nanoscaffolding is typically substantially equivalent to the rate at which the biodegradable scaffolding material is degraded in vivo. For example, the low dimension $MnO_2$ nanoscaffolds of the present disclosure may be controlled to degrade rapidly, with full degradation in three days, or slowly, with around 20% degradation after 2 weeks. This wide range tunable and therapeutic relevant degradation profile illustrates the utility of the nanoscaffolds for transplanting stem cells to treat central nervous system injuries, as well as for tissue engineering in general. For example, without wishing to be bound by theory, fast degradation may not be beneficial for treating spinal cord injury (SCI). On the other hand, regarding cell transplantations, a slow biodegradability is known to restrict cell migration and proliferation, and lead to nutrient and oxygen deficiencies for cells, in which case fast degradation is desired. Accordingly, the nanoscaffolds of the present disclosure can be used for rationally guided drug selection and scaffold design, optionally using computer simulations (for example, DFT simulations used in the Examples). This ability to tune the rate of biodegradation, and thus the rate of release of therapeutic agents and cells, offers an advantage, for example, over graphene and graphene oxide nanosheets, which do not biodegrade.

The rate at which the biodegradable low dimension $MnO_2$-containing nanoscaffolding material is degraded in vivo can be measured by detecting the release of $Mn^{+2}$ ions from the biodegradable scaffolding material (for example by MRI or FRET). The nanoscaffolds release $Mn^{+2}$ on degradation, producing an MRI-detectable signal which can be used to quantify the degradation rate. As noted above, the rate at which the therapeutic agent or cells are released from the biodegradable nanoscaffolding, is typically substantially equivalent to the rate at which the biodegradable scaffolding material is degraded in vivo. Thus, the rate at which the therapeutic agent is released is measurable, by quantifying the rate/amount of $Mn^{+2}$ released. Additionally, because $Mn+2$ is similar to $Ca+2$, it may be internalized by cells and retained, rather than being cleared immediately. Low dimension $MnO_2$ support structures also serve as fluorescent quenchers and enable detection of degradation and drug release with Fluorescence Resonance Energy Transfer (FRET).

The nanoscaffolds of the present disclosure may be used to treat, or prevent a disease or disorder in a subject in need thereof. In one embodiment of the invention, the nanoscaffolds may be surgically implanted, for example by grafting or inserting, into the subject. In a different embodiment, the nanoscaffolds may be injected into the subject. Whether implanted or injected, the nanoscaffolds would typically contain at least one therapeutic agent, such as those described herein-above. The diseases or disorders which the nanoscaffolds of the present disclosure can be used to treat are explicitly not limited. The examples presented herein show treatment of spinal cord injury (SCI), however, this is only one possible application. Other diseases/disorders comprise any of congenital disorders, neurological disorders, muscular disorders, metabolic disorders, autoimmune disorders, cellular proliferative disorders, e.g. neoplasms or cancers, viral infections, bacterial infections, protist infections, fungal infections, acute tissue injuries/trauma, chronic tissue injuries/trauma, and combinations thereof. Explicitly non-limiting examples of diseases/disorders for which the nanoscaffolds may be used in treatment include, abdominal aortic aneurysm, acne, acute cholecystitis, acute lymphocytic leukemia (ALL), acute myeloid leukemia (AML), acute pancreatitis, Addison's disease, alcoholism, allergic rhinitis, Alzheimer's disease, anal cancer, angioedema, ankylosing spondylitis, anorexia nervosa, arthritis including rheumatoid arthritis, asthma, atopic eczema, bile duct cancer, bipolar disorder, bladder cancer, blood cancer, blood poisoning, bone cancer, bone marrow cancer, bowel cancer, bowel polyps, brain stem disorders, brain tumors, breast cancer, bronchiectasis, bronchitis, bursitis, burns, cellulitis, cervical cancer, chest infections, chronic kidney disease, chronic pancreatitis, chronic myeloid leukemia (CML), chronic obstructive pulmonary disease (COPD), *Clostridium difficile* infection, congenital heart diseases, costochondritis, Crohn's disease, cystic fibrosis, cystitis, deep vein thrombosis (DVT), dementia with Lewy bodies, dental abscesses, diabetes (Type I and II), diabetic retinopathy, diverticulitis, erectile dysfunction, Ewing sarcoma, fibroids, fibromyalgia, gallbladder cancer, ganglion cysts, germ cell tumors, hairy cell leukemia, head and neck cancer, heart failure, hearing loss, hepatitis A, B, and C, hyperlipidemia, high cholesterol, HIV/AIDS, Hodgkin lymphoma, Non-Hodgkin lymphoma, hyperglycemia, hypoglycemia, hyperhidrosis, idiopathic pulmonary fibrosis, iron deficiency anemia, irritable bowel syndrome (IBS), Kaposi's sarcoma, kidney cancer, kidney failure, kidney infection, labyrinthitis, Langerhans cell histiocytosis, laryngeal cancer, liver cancer, liver disease, liver tumors, lung cancer, lupus, Lyme disease, malaria, malignant brain tumors, meningitis, mesothelioma, migraines, multiple myeloma, multiple sclerosis (MS), nasal and sinus cancer, nasopharyngeal cancer, neuroblastoma, neuroendocrine tumors, non-alcoholic fatty liver disease (NAFLD), obesity and related disorders, organ failure, osteoarthritis, osteoporosis, osteosarcoma, ovarian cancer, ovarian cysts, overactive thyroid disorders, pancreatic cancer, Parkinson's disease, penile cancer, peripheral neuropathy, pneumonia, polymyalgia rheumatic, prostate cancer, psoriasis, psoriatic arthritis, psychiatric disorders, reactive arthritis, retinoblastoma, rhabdomyosarcoma, rosacea, septic shock, sexually transmitted infections (STIs), sickle cell disease, Sjogren's syndrome, skin cancers, spinal cord injury (SCI), stomach cancer, testicular cancer, thyroid cancer, ulcerative colitis, vaginal cancer, vulvar cancer, Wilms tumor, any related disorders, and combinations thereof.

There are a number of methods to make the biodegradable nanoscaffolds of the present disclosure, and the nanoscaffolds are explicitly not limited to any particular methods disclosed herein. In one embodiment of the invention, the biodegradable nanoscaffolds may be made according to a "vacuum filtration" method, disclosed in the Examples in detail. In this embodiment, a first solution containing a plurality of low dimension manganese dioxide support structures, for example, 2D $MnO_2$ nanosheets, or 1D $MnO_2$ nanotubes or nanorods, may be provided. Next, but not necessarily, one or more therapeutic agents and/or cells, as described herein-above, may be added to the first solution. If the therapeutic agents have amine and/or aromatic residues, they may self-assemble with the low dimension manganese dioxide support structures. Next, a second solution containing a plurality of ECM proteins and/or cationic polymers (as described herein-above), may be mixed with the first solution, forming a mixture. The ECM proteins and/or cationic polymers will spontaneously self-assemble with the low dimension manganese dioxide support structures, typically in under five (5) seconds, as evidenced by the Examples. Next, but not necessarily, centrifugation followed by re-suspension may occur. Finally, but not necessarily, the resultant mixture may be submitted to vacuum filtration, in order to isolate the biodegradable nanoscaffolds, which are optionally loaded with one or more therapeutic agents and/or cells.

In a different embodiment of the invention, the low dimension manganese dioxide support structures, and the ECM proteins and/or cationic polymers are mixed in a buffer solution, optionally with at least one therapeutic agent and/or cells. The low dimension manganese dioxide support structures self-assemble in the buffer solution, with the ECM proteins and/or cationic polymers. This results in a mixture, containing self-assembled low dimension manganese dioxide support structures, which is suitable for injection in a subject in need thereof. In this embodiment, it is preferred that the ratio of ECM proteins and/or cationic polymers to low dimension manganese dioxide support structures in solution is higher than 1:10. Suitable buffer solutions include, for example phosphate buffered saline, NaCl buffer, lithium salt solution, iron (II) and/or iron (III) salt solution, zinc salt solution, calcium salt solution, Lactated Ringer's buffer, Plasma, Sterofundin, 5% glucose buffer, sodium bicarbonate buffer, MES buffer, HEPES buffer, Bis-tris methane buffer and sodium acetate buffer.

In a further embodiment, at least one cell is added to a support structure solution containing a plurality of zero-dimension, one-dimension and two-dimension manganese dioxide support structures. Droplets of a cationic polymer solution having a polymer concentration of greater than 30 mg/ml, is added to the support structure solution. The low dimension manganese dioxide support structures, and the ECM proteins and/or cationic polymers are mixed in a buffer solution, optionally with at least one therapeutic agent and/or cells. In one embodiment of the invention, the cationic polymer used in the aforementioned method is an ECM polysaccharide.

As used herein, the term "antibody" (Ab) is used in the broadest sense, and specifically may include any immunoglobulin, whether natural, or partly, or wholly synthetically produced, including, but not limited to monoclonal antibodies, polyclonal antibodies, multispecific antibodies (for example, bispecific antibodies and polyreactive antibodies), and antibody fragments. Thus, the term "antibody," as used in any context within this specification, is meant to include, but not be limited to, any specific binding member, immunoglobulin class and/or isotype (e.g., IgG1, IgG2a, IgG2b, IgG3, IgG4, IgM, IgA1, IgA2, IgD, and IgE), and biologically relevant fragment, or specific binding member thereof, including, but not limited to, Fab, $F(ab')_2$, scFv (single chain or related entity) and (scFv) 2.

As used herein, the term "biologic drug" may refer to an antibody coupled to a therapeutic agent, or antibody coupled to a therapeutic drug or agent, via a degradable or cleavable linker, e.g. an antibody-drug conjugate (ADC). ADC technology is known in the art, and is covered in, for example, Beck et al. Nature Reviews Drug Discovery 16, 315-337 (2017), hereby incorporated by reference in its entirety.

As used herein, the term "cytokine" may refer to any substances secreted by cells of the immune system that have an effect on other cells, including both anti-inflammatory and pro-inflammatory cytokines. Exemplary cytokines include, but are not limited to, those in the IL-1 superfamily, TNF superfamily, interferons, chemokines, and IL-6 superfamily, as well receptors of any cytokines.

As used herein, the term "nucleic acid," may refer to a polymer composed of a multiplicity of nucleotide units (ribonucleotide, deoxyribonucleotide, or related structural variants) linked via phosphodiester bonds, including but not limited to, DNA or RNA. The term encompasses sequences that include any of the known base analogs of DNA and RNA. Examples of a nucleic acid include, and are not limited to, mRNA, miRNA, tRNA, rRNA, snRNA, siRNA, dsRNA, cDNA and DNA/RNA hybrids. Nucleic acids may be single stranded or double stranded, or may contain portions of both double stranded and single stranded sequences. The nucleic acid may be DNA, both genomic and cDNA, RNA, or a hybrid, where the nucleic acid may contain combinations of deoxyribo- and ribo-nucleotides, and combinations of bases including uracil (U), adenine (A), thymine (T), cytosine (C), guanine (G), and their derivative compounds. Nucleic acids may be obtained by chemical synthesis methods or by recombinant methods. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof.

As used herein, the term "patient" or "subject" may be used interchangeably. A "subject" may refer to a biological system to which a treatment can be administered. A biological system can include, for example, an individual cell, a set of cells (e.g., a cell culture), an organ, a tissue, or a multi-cellular organism. A "patient" or "subject" can refer to a human patient or a non-human patient.

As used herein, the term "peptide" may refer to peptide compounds containing two or more amino acids linked by the carboxyl group of one amino acid to the amino group of another, to form an amino acid sequence. Peptides may be purified and/or isolated from natural sources or prepared by recombinant or synthetic methods. A peptide may be a linear peptide or a cyclopeptide, i.e. cyclic, including bicyclic. A "cyclic peptide" or "cyclopeptide," as used herein, may refer to a peptide having at least one internal bond attaching nonadjacent amino acids of the peptide. A "bicyclic peptide" may have at least two internal bonds forming a cyclopeptide.

As used herein, the term "small molecule" may refer to non-peptidic, non-oligomeric organic compounds, either synthesized or found in nature. These compounds may be "natural product-like," however, the term "small molecule" is not limited to "natural product-like" compounds. Small molecules are typically characterized in that they possess one or more of the following characteristics: several carbon-carbon bonds, multiple stereocenters, multiple functional groups, at least two different types of functional groups, and a molecular weight of less than 1500, although not all, or even multiple, of these features need to be present.

As used herein, the term "treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. The terms "prevent" or "preventing" refer to prophylactic and/or preventative measures, wherein the object is to prevent, or slow down the targeted pathological condition or disorder. In addition, "treating" or "treatment" does not require complete alleviation of signs or symptoms, does not require a cure, and specifically includes protocols that have only a marginal effect on the patient.

As used herein, and in the appended claims, the singular forms "a", "and" and "the" include plural references, unless the context clearly dictates otherwise.

The term "about" refers to a range of values which would not be considered by a person of ordinary skill in the art as substantially different from the baseline values. For example, the term "about" may refer to a value that is within 20%, 15%, 10%, 9%, 8%, 7%, 6%, 5%, 4%, 3%, 2%, 1%, 0.5%, 0.1%, 0.05%, or 0.01% of the stated value, as well as values intervening such stated values. Context will dictate which value, or range of values, the term "about" may refer to in any given instance, throughout this disclosure.

Where a value of ranges is provided, it is understood that each intervening value, between the upper and lower limit of that range, and any other stated or intervening value in that stated range, is encompassed within the invention. The upper and lower limits of these smaller ranges, which may independently be included in the smaller ranges, is also encompassed within the invention, subject to any specifically excluded limit in the stated range.

Each of the applications and patents cited in this text, as well as each document or reference, patent or non-patent literature, cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference in their entirety. More generally, documents or references are cited in this text, either in a Reference List before the claims; or in the text itself; and, each of these documents or references ("herein-cited references"), as well as each document or reference cited in each of the herein-cited references (including any manufacturer's specifications, instructions, etc.), is hereby expressly incorporated herein by reference.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

The following non-limiting examples serve to further illustrate the present invention.

EXAMPLES

The following examples describe the synthesis and characterization of the biodegradable hybrid low dimension $MnO_2$ nanoscaffolds, as well as their use in stem cell therapy and as a drug delivery platform. Example 1 relates to the materials and methods utilized in Examples 2-6.

Example 1. Synthesis and Characterization of the Biodegradable Hybrid $MnO_2$ Nanoscaffolds Synthesis and Characterization of 2D $MnO_2$ Nanosheet and Graphene Oxide:

2-D $MnO_2$ nanosheets were synthesized as described in Kai, K. et al. Room-temperature Synthesis Of Manganese Oxide Monosheets. *J. Am. Chem. Soc.* 130, 15938-15943, (2008), hereby incorporated by reference in its entirety.

Briefly, 2.2 g tetramethyl ammonium pentahydrate (TMAOH·5H$_2$O, Alfa Aesar) was first dissolved in 20 mL of 3% wt. H$_2$O$_2$ (Sigma-Aldrich) by vortexing (concentration of TMAOH is 0.6 M). In parallel, 0.594 g MnCl$_2$·4H$_2$O (Sigma-Aldrich) was dissolved in 10 mL de-ionized water (0.3 M MnCl$_2$) through sonication. The TMAOH dissolved in H$_2$O$_2$ solution was rapidly added into MnCl$_2$ solution, within 10 seconds, with fast stirring at 1200 rpm. The solution was stirred at 600 rpm overnight, and centrifuged at 4000 rpm for 5 minutes, to obtain the bulk δ-MnO$_2$. After washes with water and 2 washes with ethanol, combined with shaking and centrifuge, bulk MnO$_2$ was dried in the oven, under ambient conditions, for 12 hours. After adding 100 mg of MnO$_2$ into 10 mL de-ionized water, the solution was extensively sonicated for 10 hours. Lastly, the solutions were centrifuged at 8000 rpm for 10 minutes to get rid of the aggregations and un-exfoliated products. The black-colored MnO$_2$ solution was measured with concentration by evaporating water in the solution. The 2D MnO$_2$ nanosheets were diluted to 10 µg/mL for TEM (80 Kv on a Philips CM12 with an AMT digital camera model XR111) and Ultra-Stem imaging. For X-ray photoluminescence spectroscopy (Thermo Scientific ESCALAB 250 Xi with a base pressure <1*10$^{-9}$), the 2D MnO$_2$ nanosheet solution (100 µg/mL) was drop-casted onto a silicon substrate and dried in a vacuum. An Al-Kα monochromated X-ray source was used to obtain the core level spectra and the instrumental broadening was around 0.5 eV. The hydrodynamic size and zeta potential of the 2D MnO$_2$ nanosheets in aqueous solution were measured by a ZS (Nano Zetasizer) dynamic light scattering instrument (Malvern Instruments, Malvern, UK), with temperature set to 25° C., and a detection angle at 90 degrees. The UV-vis absorption spectrum of the MnO$_2$ nanosheet solution was measured by a Varian Cary 50 spectrophotometer, using a quartz cuvette.

Graphene oxide was synthesized as described in Kim, T.-H. et al. Controlling Differentiation Of Adipose-Derived Stem Cells Using Combinatorial Graphene Hybrid-Pattern Arrays. *ACS Nano* 9, 3780-3790, (2015), hereby incorporated by reference in its entirety. Briefly, 1.0 g of graphite (Bay Carbon) was pre-oxidized in a mixture of sulfuric acid (Sigma-Aldrich, 98%), phosphor oxide (Sigma-Aldrich) and potassium persulfate (Sigma-Aldrich), at 80° C. overnight. Next, the pre-oxidized graphite was washed with water, dried and reacted with sulfuric acid and potassium permanganate, through a 3-step process. After quenching with H2O$_2$, a shining gold solution appeared, and the graphite oxide was purified with a 10% HCl solution (Sigma-Aldrich) and water. Lastly, graphite oxide was exfoliated into graphene oxide by tip sonication (Branson). Multi-layered graphene oxide was centrifuged down at 11,000 rpm for 45 min, and the final suspension of single or few layered graphene oxide was obtained.

Measurement of 2DMno2 Nanosheet Degradation in Solution

A series of PBS solutions containing different ascorbic acid concentrations (Sigma-Aldrich, 0 µg/mL, 10 µg/mL, 50 µg/mL, 100 µg/mL, 200 µg/mL, 500 µg/mL) were first prepared. 10 µL of 3 mg/mL 2D MnO$_2$ nanosheet solution was added to each solution (3 mL), and the absorbance peak of MnO$_2$ nanosheet solution at 385 nm was used to quantify the amount of 2D MnO$_2$ nanosheet remaining in the solution. Measurements were taken at one-minute intervals for 10 minutes. The percentage of 2D MnO$_2$ nanosheet remaining was calculated by normalizing to the MnO$_2$ nanosheet absorption intensities at 385 nm at PBS solutions (MnO$_2$ nanosheet concentration of 0 µg/mL).

Measurement Of Protein Absorption By MnO$_2$ Nanosheet

10 µL of MnO$_2$ nanosheet aqueous solution and graphene oxide solution (3 mg/mL), or a piece of glass (control), was added was inserted into solutions of ECM protein (laminin protein from Sigma-Aldrich, stock concentration of 200 µg/mL, 0.5 mL, PBS is from Thermo Fisher). The solutions immediately turned brown, and continued to incubate under 37° C. for 1 hour. The solution was centrifuged 3 times at 8000 rpm for 10 min. and precipitates were removed each time until there were no visible precipitates any more, in order to remove the 2D MnO$_2$ nanosheets and graphene oxide with absorbed proteins. 0.1 mL supernatant solution was transferred into a 96-well plate, and BCA (bicinchoninic acid assay, Thermo Fisher) was used to quantify the percentage of protein absorbed on nanosheets, by subtracting the total amount of proteins remaining in the control group from the protein remaining in the experimental groups. The assay was conducted strictly following the protocols from Thermo Fisher, and absorption at 570 nm was used to quantify the protein amount for each group. These experiments were replicated 3 times, and the values were normalized to the glass control.

Micro-Contact Printing of 2D MnO$_2$ Nanosheet and Degradation of MnO$_2$ Nanosheet Pattern Photoresist (PR) micropatterns were generated on a Silicon wafer based on the photolithographic technique. Then, silicon coated with photoresist micropattern was deposited on a layer of (heptadecafluoro-1,1,2,2-tetrahydrocecyl) trichlorosilane for 2 h in a desiccator. PDMS (Sylgard 184 silicone elastomer base and curing reagent) was then poured into pre-coated photoresist patterns, and kept in a 60° C. oven for curing. The PDMS mold with micro-patterns was then detached from the photoresist and treated with oxygen plasma (1.5*10$^{-1}$ Torr, 25 seconds). A 2D MnO$_2$ nanosheet solution at 2.0 mg/mL was dropcast on a PDMS stamp, and spin coated at 500 rpm for 10 seconds, 1500 rpm for 20 seconds and 3000 rpm for 30 seconds. At the same time, a glass substrate (gold and/or silicon would work as well) was treated with oxygen plasma (Femto Science, Cute series) for 1 min. Then, the PDMS stamp coated with 2D MnO$_2$ solution was tilted and pressed on the glass substrate. After 1 min., a pressure of 75 g/cm$^2$ was mounted on PDMS stamps for 20 minutes. The 2D MnO$_2$ nanosheet patterned glass was washed with ethanol and water, and imaged under optical microscope. To monitor the degradation of 2D MnO$_2$ nanosheet micropatterns on glass, the substrate was incubated with ascorbic acid (50 g/mL) solution, and images were taken before and after solution treatment. Field Emission Scanning Electron Microscopy (FESEM, Zeiss Sigma) was used for micrograph acquisition, and Electron Dispersive X-ray (EDX) was also used to detect surface changes of the substrate before and after ascorbic acid treatment, under identical parameters.

Rat Neural Stem Cell (rNSC) Culture

Rat neural stem cells, and the required culture media, were purchased from Millipore (SCR080). The culture of rNSCs was followed strictly, according to the protocol of the manufacturer. Tissue culture vessels were treated with 20 µg/cm$^2$ of Poly-L-Lysine (Sigma-Aldrich) and 7 µg/cm$^2$ of laminin (Life Technologies) for 6 hrs at room temperature, and 4 hrs at 37° C., respectively. All cells were maintained in a humidified 37° C. incubator, with 5% CO$_2$. All experiments were conducted on cells between passage 3 and 5. rNSCs were seeded at 33K cells per cm$^2$. Cell culture media was supplemented with basic fibroblast growth factor (bFGF, 20 ng/mL), to maintain rNSCs in stem cell state. bFGF was withdrawn from cell culture media once the tissue culture vessel reached full confluency of rNSCs, to induce differentiation. Fresh media change occurred every two days.

Human Neural Progenitor Cell (hNPC) Culture

Human neural progenitor cell (hNPC) line was purchased from Millipore (SCC008), and cultured according to the manufacturer's protocol. Tissue culture vessels were treated with 20 µg/cm² of Poly-L-Lysine (Sigma-Aldrich) and 7 µg/cm² of laminin (Life Technologies) for 6 hrs at room temperature, and 4 hrs at 37° C., respectively. All cells were maintained at 37° C. in a humidified incubator with 5% $CO_2$. All experiments were conducted on passage number 3 and 5 cells. The hNSCs were seeded at 33K cells per cm² in hNSC specific media (from Millipore), supplemented with basic fibroblast growth factor (bFGF, 20 ng/mL), and epidermal growth factor (EGF, 20 ng/mL), with media exchanges occurring every other day. Neural differentiation of hNPC was achieved with the withdrawal of bFGF and EGF. The TuJ1 gene was checked for successful neuronal differentiation through use of qPCR.

Human Induced Pluripotent Stem Cells Derived Neural Progenitor Cells (iPSC-NPC) Culture Human iPSC-NPCs were derived from human iPSCs (WT126 clone 8; and WT33 clone 1), as described by publication of Marchetto, M. C. N. et al. A Model for Neural Development and Treatment of Rett Syndrome Using Human Induced Pluripotent Stem Cells. *Cell* 143, 527-539, (2010), hereby incorporated by reference in its entirety. iPSC-NPCs were expanded in a proliferation media containing DMEM/F12, with GLUTAMAX™ (Invitrogen), B27-supplement (Invitrogen), N2 (Stem Cells), and 20 ng/mL FGF2 (Invitrogen). Tissue culture vessels were treated with MATRIGEL® (Corning) with 1:200 dilution with DMEM (Invitrogen), at 37° C. for 1 hr. Similar to the rNSC protocol, bFGF was removed to start the neuronal differentiation process. Fresh media was exchanged every other day, and qPCR was used to confirm neuronal differentiation.

Immunocytochemistry

All fluorescence images were obtained using a Nikon T2500 inverted fluorescence microscope. Following generation of mature neurons, media was removed, and the cells were fixed for 15 minutes in formalin (Sigma), followed by two washes with D-PBS. The nucleus was stained with DAPI (Life Technologies) for 30 minutes, and then washed with PBS three times. Cells were then permeabilized with 0.1% Triton X-100 in PBS for 10 minutes, and non-specific binding was blocked with 5% normal goat serum (NGS, Life Technologies) in D-PBS, for 1 hr at room temperature. Neuronal marker TuJ1 was stained using the mouse monoclonal antibody against TuJ1 (1:200 dilution, Covance MMS-435P). Following the manufacturer's protocol, the fixed samples were incubated overnight at 4° C. in a solution of these antibodies in PBS containing 10% NGS. After washing three times with PBS, the samples were incubated for 1 hr at room temperature in a solution of anti-mouse secondary antibody labeled with Alexa Flour 568 (1:100, Life Technologies) and DAPI (1:100, Life Technologies), in PBS containing 10% NGS, and washed with D-PBS three times thereafter.

In Vitro Biodegradation of 2D $MnO_2$ Hybrid Nanoscaffold

The in vitro degradation of 2D $MnO_2$ nanosheets in physiological conditions was examined. First, different PBS solutions with varying concentrations of vitamin C (10 µg/mL, 50 µg/mL, 100 µg/mL, 200 µg/mL, 500 µg/mL) were prepared. Then 10 µL of 3 mg/mL 2D $MnO_2$ nanosheet solution was added into 3 mL of vitamin C solution, and the UV-vis spectrum of the solution was recorded every two minutes. The percentage of nanosheet remaining was normalized to the absorption (at 385 nm) of the control group, without any vitamin C added. To study the degradation of thin layered nanoscaffold, 100 µL of 2D $MnO_2$ nanosheet solution (1.0 g/mL) was dropcast into the wells of a 24 well plate treated with oxygen plasma. After vacuum drying for 3 hours, a homogeneous, yellow and transparent film formed. Then, the wells were coated with laminin, and seeded with human neural stem cells, at a cell density of 80 k/well. The cells were cultured in normal differentiation media (without bFGF and no exogenous compounds), for different periods of time (1 day, 3 days, 7 days, 12 days, 17 days, and 22 days). The cells were then fully detached, using acutase, for 10 minutes at 37° C. This was followed by washing with PBS and de-ionized water, and then the 24-well plate was vacuum dried. Based on the absorption of 2D $MnO_2$ nanosheets at 385 nm, the degradation percentage was quantified by subtracting background (empty well) and normalizing to the well without culturing the cells.

To study the degradation of thick layered nanoscaffold, a 3-layer, cell-2D $MnO_2$ nanoscaffold-cell sandwiched structure that mimics tissue structures was formed, through centrifugation at 1300 rpm, in a 15 mL Eppendorf centrifuge tube. A similar structure of graphene oxide (GO) nanoscaffold-cell construct was formed, using the same protocols, as a control. The first layer contained 1 million iPSC-NSCs. The second layer contained 1.0 mg of 2D $MnO_2$ nanosheets or graphene oxide. The third layer (Top layer) was centrifuged down from another 1 million iPSC-NSCs. Degradation of the scaffolds was monitored by the volume change and thickness change of scaffold on a weekly base. Based on the assumption that the scaffold had identical radius and areas, the percentage of scaffold volume was normalized to the thickness that was measured on Day 1.

To demonstrate that cell-seeded nanoscaffold can degrade quickly under biocompatible redox conditions, an aqueous solution of 0.3 mg/mL $MnO_2$ nanosheet was filtered through a cellulose membrane, then a layer of dye-labeled (food dye) cells was formed on the 2D $MnO_2$ nanosheet assembled substrate, using a tri-circular PDMS chamber. After the addition of 20 mg/mL ascorbic acid (Sigma-Aldrich) for 5 minutes, most of the dark color of the 2D $MnO_2$ nanosheets disappeared, and a layer pink colored cell layer was formed.

The viability of iPSC-NSCs under different ascorbic concentrations was measured by presto blue cell viability assay. MATRIGEL® (Millipore) was first coated into 48-well plates. Then, the iPSC-NSC was seeded into each well, at a cell density of 50 k in growth media (bFGF added). After the cells were attached and stabilized for overnight, different amounts of ascorbic acid dissolved in cell media was then added into different groups, to make final concentrations of 0 µg/mL (control), 100 µg/mL, 500 µg/mL, 1 mg/mL, 5 mg/mL, 10 mg/mL, 20 mg/mL, 50 mg/mL, and 100 mg/mL. At each concentration, two periods of time for ascorbic acid treatment were also included: 10 minutes and 30 minutes. After ascorbic acid treatment, cell media was changed to growth media, and continued to culture for 48 hours. The cell viabilities under different ascorbic acid concentrations and time points were quantified fluorescence (excitation at 570 nm and emission at 590 nm) presto blue assay and normalized to the control group (no ascorbic acid treatment).

Fabrication And Characterization Of $MnO_2$ Hybrid Nanoscaffold

To fabricate the 2D $MnO_2$ hybrid nanoscaffolds, 10 mL of 2D $MnO_2$ nanosheet solution, at a specific concentration, was filtered through a cellulose filter paper (diameter=20 nm), under vacuum conditions. Then, the filter paper was taken out and cut into sizes and shapes of choice. To transfer onto a transparent glass substrate, cleaned glass was first treated with oxygen plasma, then the filter paper bearing the 2D $MnO_2$ nanosheets was wetted with de-ionized water and pressed against glass. A 2.0 kg/cm$^2$ pressure was placed on top of the filter paper for 8-12 hours, after which the glass attached to the 2D $MnO_2$ nanosheets was detached from the weight. To remove the cellulose attached with the nanoscaffold, the substrate was incubated in acetone for 0.5 hour, and then briefly washed in methanol for 1 hour. The transparency of the nanoscaffold was easily tuned by using different concentrations of 2D $MnO_2$ nanosheet solution. The concentrations used were 100 μg/mL and 200 μg/mL. For cellular studies, a concentration of 200 μg/mL was used throughout the study. Graphene oxide assembled scaffolds were fabricated using an identical protocol, with a graphene oxide aqueous solution of 200 μg/mL. FESEM was used to characterize the nanoscaffold.

To study the ability of the nanoscaffold for covalent conjugation, an ethnolic solution of amino propyl triethoxysilane (APTES, Sigma-Aldrich) was used for conjugation. Nanoscaffold was incubated in 1.0 mg/mL APTES solution for 1 hour, and then washed with ethanol 3 times and water 3 times. Then the APTES functionalized substrate was incubated in 1.0 mg/mL fluorescamine (Sigma-Aldrich) solution (ethanol solution) for 4 hours. Fluorescamine selectively reacts with the amine group on the APTES functionalized nanoscaffold and forms a fluorescent compound. After washing with ethanol and water a few times, the substrate was imaged under fluorescent microscope. The blue fluorescence from the substrate indicated the chemical functionality of nanoscaffold towards APTES.

Quantification of ECM protein (laminin) absorbed on the 2D $MnO_2$ nanosheets was carried out by measuring the laminin concentration before, and after 2D $MnO_2$ nanosheet absorption. 200 μL of 80 μg/mL laminin solution was incubated with 2D $MnO_2$ nanosheets (1 mg, 1 mL), graphene oxide (1 mg, 1 mL) and glass for 1 hour under 37 degree. Then, the solution was centrifuged to remove the 2D $MnO_2$ nanosheets, graphene oxide and glass. The laminin concentration before and after 2D $MnO_2$ nanosheet absorption was quantified by a BCA protein assay (Thermo Fisher), and absorbance at 562 nm was used for the plate reader. The amount of laminin absorbed on the 2D $MnO_2$ nanosheets was calculated by subtracting the laminin concentration after 2D $MnO_2$ nanosheet absorption, from the original concentration. The percentage of laminin absorption was calculated by dividing the amount of laminin absorbed by the original laminin concentration.

In the case of the laminin-nanoscaffold, 400 μL of 2D $MnO_2$ nanosheet aqueous solution (2 mg/mL) was quickly added into 100 μL of laminin solution (10 μg/mL, PBS, PH=7.4). Then, the laminin conjugated 2D $MnO_2$ nanosheet was centrifuged, and re-suspended in 10 mL de-ionized water (2D $MnO_2$ nanosheet concentration was 80 μg/mL). After vacuum filtration, the cellulose filter paper was cut into sizes and shapes of interest for the cell culture studies.

To synthesize the 1D $MnO_2$ nanotubes, a hydrothermal method was used. Briefly, 0.1 g potassium permanganate was mixed with 0.2 ml concentrated HCl (37%) and 11 ml deionized water. Then the solution was stirred and added into a 15 ml Teflon hydrothermal chamber. After heating at 140 celcius overnight, the solution was cooled down and the dark-colored precipitates in the Teflon chamber were collected, washed and re-dispersed in deionized water.

To synthesize the 1D $MnO_2$ nanorods, a co-precipitation method at room temperature was used. 1.0 gram of tetramethylammonium pentahydrate was first dissolved in a 20 ml 3% H2O2 solution, then mixed with 10 ml 0.3 mol/L MnCl2 tetrahydrate followed by vigorous stirring. 12 hours after the reaction, the precipitates were washed by water and ethanol. Then the brown precipitates were dried in the oven overnight followed by a brief sonication in a water solution.

To synthesize 1D $MnO_2$ nanotubes or nanorods assembled scaffolds, the 1D nanostructures were first coated with 20 mg/ml of gelatin in PBS. After coating overnight, free gelatin was removed by centrifugation of the 1D $MnO_2$ nanostructures at 10000 rpm for 10 minutes followed by washing with water. Afterwards, the gelatin coated 1D $MnO_2$ can be assembled into scaffolds either by vacuum filtration, dropcasting, centrifugation or self-assembly with or without cells under buffer conditions, which are similar processes comparing to the formation of 2D $MnO_2$ nanosheets-based scaffolds.

Differentiation of iPSC-NSC on $MnO_2$ Hybrid Nanoscaffold and Control Scaffolds:

The viabilities of iPSC-NSCs, rat neural stem cells (rNSC) and human neural progenitor cells (hNPC) cultured on 2D $MnO_2$ nanoscaffolds were measured by presto blue cell viability assay. Into 24-well plates, laminin was first coated onto glass (control), graphene oxide assembled scaffold (positive control), and 2D $MnO_2$ nanoscaffolds, at a concentration of 20 μg/mL, for 4 hours. Then the iPSC-NSC was seeded into each well, at a cell density of 20 k in growth media (bFGF added). After the cells were cultured for 48 hours, cell viabilities cultured on different substrates were quantified by fluorescence (excitation at 570 nm and emission at 590 nm), presto blue assay (Thermo Fisher), and normalized to the control group (glass).

For the differentiation of iPSC-NSC on glass substrates, 2D $MnO_2$ nanoscaffold, graphene oxide assembled scaffold (GO nanoscaffold), and glass were first sterilized in a UV lamp for 5 minutes, and then coated with laminin solution (20 μg/mL) for 4 hours. The substrates were placed in 24-well plates and iPSC-NSCs were seeded into the wells at a cell density of 60 k/well. The cells proliferated for 24 hours, and the media was changed into differentiation media, without bFGF. To observe the stem cell proliferation and attachment onto the substrate, the cells were imaged in an optical microscope (Nikon Ti series). After 7-days' differentiation, the cells were fixed, and immunostaining on nuclei (Hoechst) and neuronal marker (TuJ1) was conducted. Axon lengths for each substrate were measured, based on the immunostained cell fixatives. To quantify the neuronal markers (TuJ1) and astrocyte markers (GFAP), qRT-PCR was conducted by using GAPDH mRNA as a control.

Focal Adhesion Kinase Studies:

To study the effect of laminin density on the adhesion of iPSC-NSC, 2D $MnO_2$ nanoscaffold, GO nanoscaffold and glass were coated under identical conditions, except for the concentrations (5 μg/mL, 10 μg/mL, 20 μg/mL) during laminin solution coating. After a 3 day differentiation process, the morphology and attachment of cells were imaged under optical microscope. To further quantify focal adhesion kinase that is directly involved in the cell adherence, cells cultured on different substrates, and at different laminin concentrations, were trizoled. FAK mRNAs and GAP43 mRNAs were then quantified and normalized to GAPDH mRNAs in the qRT-PCR analysis.

Laser Interference Lithography & Cell Differentiation Studies:

A photoresist nanohole array was first generated using laser interference lithography. By using a Lloyd's mirror interferometer, the light coming from the light source (He—Cd laser, KIMMON KOHA Laser Systems, Japan) interfered with the reflected light from the mirror, based on a previous set-up. Cleaned ITO glass was first spin-coated with hexamethyldisilazane (HMDS, Sigma-Aldrich) using a spin coater (Laurell Technologies, USA), and then a diluted photoresist was spin-coated onto the HMDS coated ITO glass. After a soft baking at 125° C. for 60 seconds, the substrate was exposed to UV (325 nm, 0.8 m W) for 15 seconds. To generate PR nanohole arrays with different hole densities, the angle between the sample holder and the adjacent Lloyd's mirror was adjusted, based on the equation: $\Delta=\lambda/2 \sin\theta$ ($\Delta$: size of the pitch/nm; $\lambda$: wavelength of UV laser; $\theta$: the incident) angle/°). To fabricate nanoarrays with densities at 50%, 64%, 72%, the incident angle was adjusted to 339°, 333° and 321°. After UV exposure, the substrates were put on a hot plate (125° C., 60 seconds) for post-exposure baking. The unexposed photoresist was then removed by a developer solution for 1 minute, followed by de-ionized water washing. Hollowgram appeared at this stage.

Onto the polymeric nanohole patterned glass substrate, a plastic chamber was attached using polydimethylsiloxane (PDMS), followed by thermal curing. For the electrochemical deposition, a solution of $HAuCl_4$ (5 mM), ammonium sulfate (0.5 mM) and potassium chloride tribasic monohydrate (2 mM, Sigma-Aldrich) was used. Gold deposition was performed on a DC amperometry (Epsilon potentiostat, BASi, USA) under −1.2V for 180 seconds. After the gold deposition into the nanoholes and plastic chamber was removed, the ITO substrates were incubated in stripper solution with a water bath at 65° C. for 70 minutes. The gold nanoarrays were imaged using SEM.

Gold nanopatterns on ITO substrates with different gold array densities were then washed with acetone and water, and functionalized with RGD, by incubation in a thiol-iRGD aqueous solution (1.0 mM) for 4 hours at room temperature. Then the substrate was washed with water 3 times. Without any coating, the iPSC-NSC was seeded onto the control substrate (bare ITO without gold deposition). After culturing in growth media for 1 day, the cells were imaged in the optical microscope. Then, the cell media was changed to differentiation media with regular media change. After differentiation for 6 days, the cells were fixed and stained with HOEST and TuJ1 for fluorescent imaging.

Fabrication of $MnO_2$ Laminin Hybrid Nanoscaffold and Cell Encapsulation:

2D $MnO_2$ laminin hybrid nanoscaffolds were facilely fabricated by adding 10 μL of 2D $MnO_2$ nanosheet aqueous solution (3 mg/ml) into 100 μL of laminin solution (1 mg/ml), resulting in 2D $MnO_2$ nanosheet assembly within 5 seconds. To fabricate larger scale 2D $MnO_2$ laminin hybrid nanoscaffold, 100 μL of 2D $MnO_2$ nanosheet aqueous solution (3 mg/ml) was added into 500 μL of laminin solution (1 mg/ml), and then vacuum filtered on a cellulose paper, as described above. The structure of the $MnO_2$ laminin hybrid nanoscaffold was then analyzed in FESEM. To fabricate cell encapsulated $MnO_2$ laminin-nanoscaffold, 1 million iPSC-NSCs were centrifuged down and re-dispersed in 25 μL of laminin PBS solution. Different amounts (0, 0.3 μL, 1.5 μL, 3 μL, 15 μL and 30 μL) of 2D $MnO_2$ nanosheet solution (3 mg/ml) were injected into the cell laminin solution, and a iPSC-NSC encapsulated pellet was spontaneously formed after one hour. To investigate the morphological interaction between the $MnO_2$ and encapsulated iPSC-NSCs, the medium of mature neurons was removed and the neurons were fixed for 15 minutes in Formalin solution (Sigma-Aldrich), followed by two DPBS washes. The biological samples were then dehydrated to eliminate water, by a series of ethanol dehydration processes, by replacing PBS with 50% ethanol/water, 70% ethanol/water, 85% ethanol/water, 95% ethanol/water, and absolute ethanol, twice for 10 minutes, each in succession. The biological samples were then stored in absolute ethanol before being transferred to a critical point dryer to eliminate traces of ethanol. Then 20 nm of gold was sputter coated onto the surface of biological samples after drying. FESEM was then used for micrograph acquisition.

For the differentiation of iPSC-NSC on substrates, glass, $MnO_2$ nanoscaffold and $MnO_2$ laminin hybrid nanoscaffold were first sterilized in a UV lamp for 5 minutes, and then coated with laminin solution for 4 hours. The substrates were placed in 24-well plates and iPSC-NSCs were seeded into the wells at a cell density of 60 k/well. After 6 days' differentiation, the cells were fixed, and immunostaining on nuclei (DAPI) and neuronal marker (TuJ1) was conducted.

Calcium imaging of neurons differentiated from iPSC-NSCs on $MnO_2$ laminin hybrid nanoscaffold in 12 well-plates. iPSC-NSCs were differentiated on $MnO_2$ laminin hybrid nanoscaffold using an identical protocol to the one mentioned above for 6 days, then the cells were incubated with 1 ml of Fura-2 AM (Life Technologies, 1:200 dilution) in cell media for 1 hour. Afterwards, cell media was changed to PBS. Under the video mode of a fluorescence microscope, concentrated KCl solution in PBS (50 mM, 0.1 ml) was added into the cells, and a video was taken for 10 minutes, with 60 frames per seconds. The videos were pseudocolored, with red indicating strong calcium flux and green indicating weak calcium flux. An identical procedure was also applied for collecting calcium imaging of neurons differentiated from hNPCs. Differentiation experiments were repeated under identical conditions, using immunostaining performed using anti-MAP2 and anti-synapsin 1 antibodies.

Dye Loading on $MnO_2$ Nanoscaffold and MRI Studies:

0.3 mg rhodamine B (Alfa Aesar) was added into 3.0 ml of 2D $MnO_2$ nanosheet solution. After incubation at room temperature for 12 hours, 5.0 ml PBS (PH=7.4) was gradually added into the solution, and RhB loaded 2D $MnO_2$ nanosheets were centrifuged down, at 5000 rpm for 5 minutes, and extensively washed (6 times) with PBS, to remove the residual RhB solution. Then, the RhB-loaded 2D $MnO_2$ nanosheets were re-suspended into 10 ml of solution, and re-assembled with laminin, using the identical conditions for fabricating $MnO_2$ laminin hybrid nanoscaffolds. To monitor the dye hold-up, RhB-nanoscaffold was incubated with PBS for 12 hours, then the fluorescence of the supernatant was detected in a fluorescence spectra (Varian Cary Eclipse). The dye loading was confirmed by degrading the RhB-nanoscaffold, using 1.0 mg/ml ascorbic acid PBS solution. The instant appearance of a pink color from the RhB proved the loading of RhB inside the nanoscaffold. RhB-nanoscaffold, before and after degradation, were also spotted in a glass slide in a close-proximity, and then imaged in the fluorescent microscope. To test the correlation between MRI signals and RhB released, different amounts of RhB-nanoscaffold were degraded with ascorbic acid (1.0 mg/ml) to form a homogeneous solution. Then, the same solution in 96-well plates was used for MRI (Aspect's M2™ Compact High-Performance MRI, IT) measurement and fluorescence measurement (plate reader).

To study the day-dependent drug (RhB) release from the MnO₂-laminin hybrid nanoscaffold, PBS with 10 g/ml vitamin C was used to incubate the RhB loaded nanoscaffold, and was changed regularly every day. Fluorescence images were taken at Day 1, Day 2, and Day 7, and the intensities from 3 different experiments were used to quantify the amount of RhB released. As a control, PCL polymer was dissolved with RhB and then formed into a scaffold by drying at room temperature. Then, the dye release was measured at the same time points as RhB loaded nanoscaffolds. The percentage of dye release was all normalized to the fluorescence intensity obtained at Day 1.

DAPT (N-[(3,5-Difluorophenyl) acetyl]-L-alanyl-2-phenyl]glycine-1,1-dimethylethyl ester, Tocris) was first dissolved in a PBS: DMF=9:1 solution (dimethylformamide, Sigma-Aldrich), at a concentration of 0.1 mg/ml. Then 1.0 ml of DAPT solution was quickly mixed with 100 μL of 3 mg/ml 2D MnO₂ nanosheet aqueous solution. After incubating for 12 hours, the solution was centrifuged down and washed with de-ionized water 3 times. The successful loading of DAPT onto MnO₂ nanosheet was confirmed by MALDI-TOF (Bruker, Ultraflex), based on the Na⁺-DAPT peak at 455 (molecular weight to charge ratio). Briefly, 50 μL of 2D MnO₂ nanosheets, loaded with DAPT solution, was mixed with 50 μL of gold nanoparticle solution (Ted Pella, 10 nm). Then 1 μL of the mixed solution was drop-cast onto ITO glass, and baked at 50° C. for 1 minute, to fully evaporate any water. The DAPT solution was drop-cast on the same ITO glass as a reference. The ITO glass was placed into the MALDI-TOF and exposed to laser for the analysis.

DFT Simulations on Small Molecule and MnO₂ Binding:

DFT calculations were carried out using the Quantum ESPRESSO software package. For the geometry optimization, Perdew-Burke-Ernzerhof (PBE) functional, along with D2 dispersion corrections, were used. The MnO₂ surface and the MnO₂ bound complexes were treated with DFT+U method. This is because conventional DFT functionals are unable to describe the strong correlation effect among the partially filled d states in Mn. The Hubbard parameter 'U', was introduced for the Mn 3d electrons, to describe the on-site Coulomb interaction, as given in the well-known GGA +U method. The values of U=4 eV and J=0 eV for MnO₂ were adopted. Spin-polarized calculations were performed, since bulk MnO₂ has an antiferromagnetic ground state. The electron cores were defined using ultrasoft pseudopotential for all of the elements, and were extracted from the Quantum ESPRESSO main website. For the k-point mesh, a γ-center was used. The wave function cutoff of 60 Ry, and kinetic energy cutoff of 240 Ry, were used in all of the cases studied. The Gaussian smearing was turned so that the difference between the free energy and the total energy was less than 0.005 Ry per atom. The energy convergence was set to 1×10−6 a.u., and the force convergence threshold for the ionic minimization was set at 1×10−4 a.u.

The binding energies on the MnO₂ surface were calculated for a series of small molecules (Table 1) and the DAPT drug molecule. The size of the cell was assumed to be equivalent to the size of a MnO₂ surface that has 8×8 oxygen atoms at the periphery. The box size for the simulated system was 23×23×40 Å, and periodic boundary conditions were used. This condition was chosen to mimic the 2D MnO₂ surface. Geometry optimizations were first performed for the bound complexes, with the resulting energy referred to as $E_{complex}$. Next, the structures of the isolated MnO₂ surface, and the molecule of interest, were optimized, obtaining their energies $E_{MnO2}$ and $E_{mol}$, respectively. The binding energy was defined as $E_b = E_{complex} - E_{MnO_2} - E_{mol}$. Negative $E_b$ indicated binding, while positive $E_b$ indicated repulsion to the surface.

Gene Expression Analysis:

Total RNA was extracted using TRIzol Reagent (Life Technologies), and transcribed to cDNA for quantitative PCR (qPCR) analysis. Specifically, cDNA was generated from 1 μg of total RNA using the Superscript III First-Strand Synthesis System (Life Technologies). The qPCR reactions were performed using Power SYBR Green PCR Master Mix (Applied Biosystems), on a StepOnePlus Real-Time PCR System (Applied Biosystems), with the primers specific to each of the target mRNAs (Table 2). The resulting Ct values were normalized to GAPDH. Standard cycling conditions were used for all reactions, with a melting temperature of 60 C. All primers were obtained from the PrimerBank database, purchased from IDT Technologies and listed in Table 1.

TABLE 1

Summary of binding energies (BE) between molecules with assigned functional groups and the 2D MnO₂ nanosheets as computed using DFT calculations.

| Molecules | Functional Group | Binding Energy (kcal/mol) | Intra-molecular distance (Angstroms) |
|---|---|---|---|
| CH₃Cl | —Cl | −3.55 | 3.16 |
| H₂O | — | −4.0 | 3.45 |
| CH₃F | —F | −5.10 | 2.96 |
| CH₃OH | —OH | −6.43 | 2.54 |
| CH₃COOH | —COOH | 7.26 | 3.01 |
| CH₃NH₂ | —NH₂ | −10.23 | 2.98 |
| Ph—CH₃ | —Ph | −11.66 | 3.08 |
| DAPT | Drug | −18.43 | 6.3 |

TABLE 2

Primers used for qPCR (obtained from PrimerBank database)

| Target (species) | Forward primer (5'-3') | Reverse primer (5'-3') |
|---|---|---|
| GAPDH (human) | CCGCATCTTCTTTTGCGTCG (SEQ ID NO: 1) | GCCCAATACGACCAAATCCG T (SEQ ID NO: 2) |
| TUJ1 (human) | GGTGTCCGAGTACCAGCAGT (SEQ ID NO: 3) | TTCGTACATCTCGCCCTCTT (SEQ ID NO: 4) |
| GAP43 (human) | AGGAAGATTGAGTCGCTGGA (SEQ ID NO: 5) | AACCTCCTCCTCGTGGGATC T (SEQ ID NO: 6) |
| FAK (human) | TGGTGCAATGGAGCGAGTATT (SEQ ID NO: 7) | GGGACTTCAGAGTGGAGCTG (SEQ ID NO: 8) |
| GAPDH (rat) | ATGACTCTACCCACGGCAAG (SEQ ID NO: 9) | CAGTGAACCTCCTCTGACCG (SEQ ID NO: 10) |
| TUJ1 (rat) | ACTTTATCTTCGGTCAGAGTG (SEQ ID NO: 11) | CTCACGACATCCAGGACTGA (SEQ ID NO: 12) |
| GFAP (rat) | GAGAGAGATTCGCACTCAGTA (SEQ ID NO: 13) | TGAGGTCTGCAAACTTGGAC (SEQ ID NO: 14) |

In Vivo Transplantation of MnO₂ Laminin Hybrid Nanoscaffold into a SCI Model:

The Notch1CR2-GFP transgenic mouse (*Mus musculus*) (Tzatzalos et al., 2012) was used in this study. Adult mice that were 5-6 months old were picked for the spinal cord injury experiments. No difference was observed between male or female animals, and thus the gender was not specified. During the surgery, initial anesthetization was performed with 5% isoflurane, and then maintained with 2% Isoflurane. For hemi-section, a laminectomy at T10~11 was first performed. Then, the dorsal blood vessel was burned with a cauterizer, and the spinal cord was cut from the middle line, towards the left, using a #10 scalpel. Following induction of injury, bio-materials with iPSC-NSCs was inserted into the wound site, and the surgical wound was sutured and closed in layers. The mice were returned to their cages for behavior tests using BMS standards (Basso D M, 2006, scores were rounded to a 0.5 scale). For harvest, the spinal cords from the injured animals were obtained via microsurgical dissection. They were washed in 1×PBS and fixed with 4% (w/v) paraformaldehyde for 24 hrs. Fixed tissues were washed again and then cryopreserved in 30% (w/v) sucrose for 48 hrs. Afterwards, the spinal cord tissue was embedded in cryo-preserving media (Tissue Tek® OCT compound) and kept frozen at −80° C.

The in vivo transplantation experiments were repeated on a wild type C57BL/6 mouse strain, utilizing GFP labelled iPSC-NSCs for xenografts. C57BL/6 mice is a mouse strain commonly used, and optimal for xenografts. To obtain GFP labelled cells, iPSC-NSCs were transfected with lentiviral vectors expressing GFP. Transfection efficiency (>90%) was confirmed, and strong green fluorescence from iPSC-NSCs before seeded to the scaffold for in vivo cell transplantation. The surgical and immunohistological staining procedures were kept identical as with the NotchCR2-GFP mice. In addition to the 3 main groups (control groups with injury only, nanoscaffold group with cell transplantation, n and PCL group with cell transplantation), 3 additional animal groups were added as control groups, to better support the therapeutic potential of the newly developed scaffold system: $MnO_2$ scaffold without laminin or DAPT, but with cell transplantation; $MnO_2$ nanoscaffold with laminin and DAPT, but without cell transplantation; and direct injection of GFP iPSC-NSCs with laminin. Each group was repeated on 2 animals (total mice number: 12). Consistent with the study on NotchCR2-GFP mice, all animals were sacrificed one-week post-transplantation. Differentiation was observed by DAPI, GFP, GFAP, TuJ1 staining and cell survival through caspase 3 staining.

Immunohistochemistry:

Frozen spinal cord tissue was sectioned transversely or sagittally (10-12 μm in thickness) using a cryostat (ThermoScientific) and air dried. Sections were blocked and permeablized for 1 hr in blocking buffer containing 10% donkey serum, 0.1% TritonX, and 0.1% Tween® 20, at room temperature. Afterwards, they were incubated with primary antibodies overnight at 4° C. Following three 10-min washes in PBS, sections were incubated in the blocking buffer containing corresponding fluorophore-conjugated secondary antibodies for 1 hour at room temperature. Slides were then washed three times with PBS (10-min each), stained with DAPI, and then incubated with 4 mM $CuSO_4$ in 50 mM ammonium acetate buffer for 10 min, to reduce autofluorescence. Sides were then mounted with mounting media (Vector Laboratories) right away, and images were taken within a week. The following primary antibodies were used: PH3 (1:100, rabbit polyclonal, sc-8656-R) from Santa Cruz Biotechnology, TuJ1, MBP, GFAP (1:1000, mouse monoclonal, G3893) from Sigma Aldrich. Images were captured using a Zeiss Axio Imager M1 fluorescence microscope and visualized with AxioVision 4.8.

Example 2. Enhanced Stem Cell Differentiation Using Biodegradable $MnO_2$ Hybrid Nanoscaffolds Hybrid inorganic nanomaterial-based scaffolds have been recently demonstrated to control stem-cell differentiation by providing controlled physical, chemical, and biological properties that can be utilized to regulate cell-matrix interactions. To investigate whether the biodegradable $MnO_2$ hybrid nanoscaffolds of the present disclosure have an enhanced binding affinity toward ECM proteins to promote cell adhesion, neuronal differentiation of stem cells, and neurite outgrowth through the ECM-mediated integrin signaling pathway, the interaction between 2D $MnO_2$ nanosheets and laminin proteins was investigated. Using a bicinchoninic acid (BCA) assay, a significantly increased laminin adsorption on 2-D $MnO_2$ nanosheets (7.5-fold increase) was observed compared to laminin's binding towards control glass substrates. To better understand the origin of such strong binding interactions between ECM proteins and 2-D $MnO_2$-nanosheets, the density functional theory (DFT) method was used to calculate the binding energies between the 2-D $MnO_2$-nanosheet, s and a series of functional groups commonly exhibited in ECM proteins. The calculation results showed the presence of electrostatic and polar-π interactions that contributed to the strong binding interactions of the biomolecules onto the 2-D $MnO_2$-nanosheets. For example, the binding energies for methylamine and methylbenzene were about 3-fold higher than that of water (Table 1). Considering that laminin proteins are rich in amino and aromatic functional groups, the DFT calculation results indicated that these interactions are involved in the strong binding of ECM proteins onto the 2D $MnO_2$-nanosheet. Given the extraordinarily high crystal surface of 2D $MnO_2$ nanosheets, it was speculated that the nanoscaffolds would also have strong binding interactions toward small molecule drugs that contain aromatic and amine structures. The DFT calculation approach was thus further utilized to provide insight into the laminin-induced formation of 3D $MnO_2$ hybrid nanoscaffolds, and acted as a screening method to identify neurogenic or anti-inflammatory drugs that can enhance survival and neuronal differentiation of NSCs in vitro and in vivo.

To study neuronal differentiation of stem cells using the $MnO_2$ hybrid nanoscaffolds, layer-by-layer $MnO_2$ nanoscaffold assembly (3D-$MnO_2$ nanoscaffolds) was synthesized using a vacuum filtration method that enabled the generation of highly homogeneous and reproducible 3D-$MnO_2$ nanoscaffolds. Compared to conventional 3D nanoscaffold-fabrication methods, such as spraying, drop-casting, and electrochemical deposition, the applied vacuum filtration method produced large-scale, homogeneous, free-standing, and mechanically robust 3D nanoscaffolds in a highly controllable way. The existence of surface hydroxyl groups on 2D $MnO_2$ nanosheets enabled the covalent functionality of the nanoscaffold. To perform the 3D-$MnO_2$ nanoscaffold-based stem cell assay, human induced pluripotent stem cell (hiPSC)-derived NSCs were chosen as a model system, since hiPSC-derived NSCs can be effectively translated into clinical applications for neuro-degenerative diseases and injuries. The incorporation of polymer substrate could increase the flexibility of nanoscaffold during cell transplantation.

By seeding hiPSC-NSCs on laminin-coated 3D-$MnO_2$ nanoscaffolds, a significant enhancement of neuronal differentiation (43% increase). and neurite outgrowth (11-fold increase). was observed. compared to the control conditions, by measuring the biomarker protein and gene expression levels. Viabilities of cells cultured on glass coated with laminin were used as controls. Cells were cultured on laminin-coated glass substrates and nanoscaffold for 2 days, and then presto-blue assay was used for quantifying relative cell viability based on the absorption at 570 nm in the plate-reader. The high cell viability of both hNPCs and iPSC-NSCs cultured on nanoscaffold indicated excellent biocompatibilities. Due to the stronger protein absorption on graphene oxide assembled scaffold and nanoscaffold, higher numbers of NSCs were adhered and grown on graphene oxide assembled scaffold and nanoscaffold compared to glass substrates.

A similar trend, with significantly enhanced neuronal differentiation, was also found in a different neural stem cell line derived from non-human mammals, indicating the wide applicability of the nanoscaffold for guiding stem cell differentiation. Similar to iPSC-NSCs cultured on nanoscaffold, Tuj mRNAs were significantly upregulated by 2.5-fold. Astrocyte markers, on the other hand, were also upregulated by 1.7-fold for rNSCs cultured on nanoscaffold. Consistent with iPSC-NSCs differentiated on nanoscaffold, a higher population of rNSCs was differentiated into neurons, compared to glass substrate. All of the substrates were coated with laminin, with identical concentrations. To understand the underlying mechanism of the 3D-$MnO_2$ nanoscaffold-based enhanced neuronal differentiation and neurite outgrowth, the pertinent laminin-mediated focal adhesion-dependent signaling pathways were investigated using a qRT-PCR (quantitative reverse transcription-polymerase chain reaction) technique. A substantial increase of focal adhesion kinase (FAK) gene (4.7-fold) and an upregulation of a neuronal growth cone-associated GAP43 gene (36%) were observed from hiPSC-NSC-derived neurons on 3D $MnO_2$ nanoscaffolds, compared to those cultured on a glass substrate. Varying laminin coating concentrations was found to significantly influence the adhesion of iPSC-NSC for all of the different substrates. However, under low laminin coating concentrations (0.5× and 1×), cells seeded on $MnO_2$ nanoscaffold, and GO nanoscaffold, showed obviously improved cell spreading and adhesion. This enhanced adhesion on $MnO_2$ nanoscaffold and GO nanoscaffold was attributed to increased protein deposition on the surface of the substrates. Increased intensities of integrin binding were found to increase numbers of cells adhered on a substrate, as well as the percentages of cells expressing neuronal markers. These results strongly suggested that the 3D-$MnO_2$ nanoscaffolds of the present disclosure can improve neuronal differentiation and neurite outgrowth, through the enhanced laminin binding and focal adhesion-related pathways.

Example 3. Controllable Biodegradation of $MnO_2$ Hybrid Nanoscaffolds Through a Redox Mechanism While low-dimensional inorganic nanomaterials have shown great potential in stem cell-based regenerative medicine, in vivo biocompatibility and biodegradation of these nanomaterials are the most critical issues to be addressed before inorganic nanomaterial-based stem cell applications can be fully realized. $MnO_2$ nanomaterials have been previously demonstrated to degrade intracellularly via a glutathione-mediated reduction reaction. However, the comprehensive biodegradation study of $MnO_2$ nanoscaffolds in extracellular microenvironments remain unexplored. As such, the degradation capability of 2D-$MnO_2$ nanosheets in phosphate buffered saline (PBS) was examined by adding extracellular bioreductants such as ascorbic acid (vitamin C).

Figure 2B:
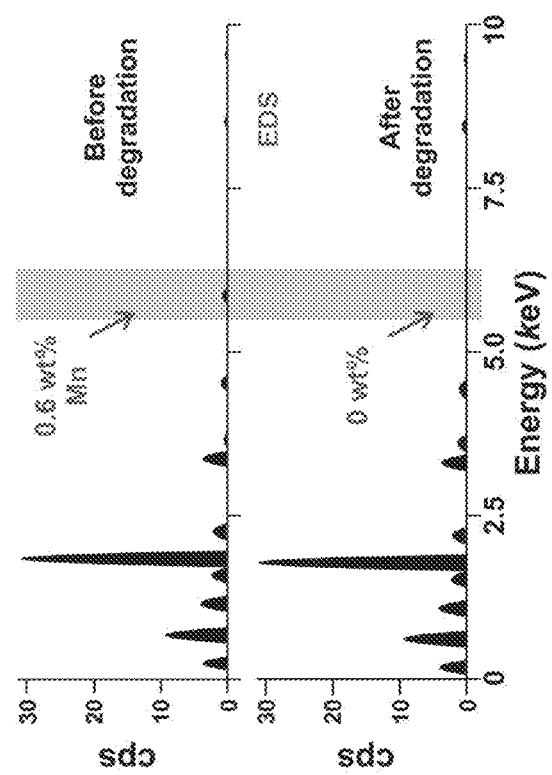
FIGS. 2A and 2B represent the controllable biodegradation of $MnO_2$ hybrid nanoscaffolds through an unconventional redox mechanism.
Figure 2A:
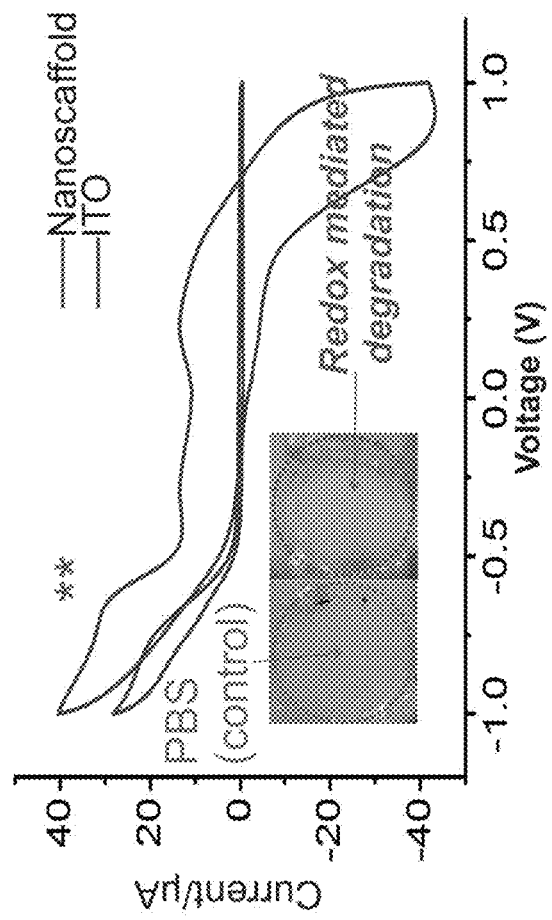

Thick layered (6 mm) nanoscaffolds, sandwiched by two cell layers, have a half-degradation time around 2 weeks. This was achieved under regular cell culture conditions, without the addition of any exogenous biochemical or vitamin. When the thickness of nanoscaffold was significantly reduced to a thin film (<1 mm), the half-degradation time was reduced to less than one week. UV-Vis absorption spectrum data confirmed that 2D-$MnO_2$ nanosheets were degraded by ascorbic acid in a dose-dependent manner. Similarly, a controllable degradation rate of 2-D $MnO_2$ nanosheets by ascorbic acid was observed using micropatterned-$MnO_2$ nanoscaffolds, by directly monitoring the disappearance of the micropatterned-$MnO_2$ nanoscaffolds and by analyzing the energy dispersive x-ray (EDX) spectrum data (FIG. 2B). Furthermore, to investigate whether the degradation mechanism of $MnO_2$ nanoscaffolds is dependent on reduction reactions alone, $MnO_2$ nanoscaffolds were placed onto a conductive Indium Tin Oxide (ITO) electrode. The redox properties of $MnO_2$ nanoscaffolds in PBS were investigated, using cyclic voltammetry (CV). A clear reduction voltage peak was detected at −750 mV from the CV curves, at which $MnO_2$ nanoscaffolds degraded within 5 minutes (FIG. 2A). These electrochemical results confirmed the hypothesis that the synthesized $MnO_2$ nanoscaffolds can be degraded via an unconventional redox-mechanism. In parallel, $MnO_2$ nanoscaffolds were inserted in between two layers of cells, which can mimic in vivo transplantation conditions, to study the nanoscaffold degradation profiles as well as to investigate whether such redox-mediated biodegradation of $MnO_2$ nanoscaffolds was possible in tissue-mimicking conditions, without adding any exogenous bioreductants or electrical stimuli. As a negative control experiment, graphene oxide (GO) nanoscaffolds were also inserted in between two layers of cells. The biodegradation of both nanoscaffolds ($MnO_2$ VS. GO) was examined daily, by measuring the thickness of the dark-colored nanoscaffold layers. Consistent with previous reports, there was no noticeable degradation of GO nanoscaffolds and neurite outgrowth through the ECM-mediated integrin signaling pathway. In contrast, $MnO_2$ nanoscaffolds rapidly degraded with over 30% of the $MnO_2$ nanoscaffolds degraded within one week, and a half-degradation time was around 2 weeks, as discussed supra. This result proved that the biodegradability of $MnO_2$ nanoscaffolds can be induced by cells without delivery of exogenous reductants. Moreover, the degradation rate of $MnO_2$ nanoscaffolds could be controlled by showing a tunable half-degradation period of from a few minutes, to one month. This tunability of a biodegradation rate was achieved by changing the assembled layered-structures of 2-D $MnO_2$ nanosheets and by controlling concentrations of reductants. In short, the $MnO_2$ nanoscaffolds represent an inorganic hybrid nanoscaffold system that can be biodegraded in vitro and in vivo. Given that the CNS microenvironment contains highly concentrated bioreductants, the controllable biodegradation properties of $MnO_2$ nanoscaffolds are more appealing and important in the field of neural tissue engineering.

Example 4. 3D $MnO_2$ Hybrid Nanoscaffolds Self-Assembled with ECM Proteins For Versatile Stem Cell Therapy One of the critical issues of conventional degradable bioscaffolds is degradation-mediated disruption of cellular microenvironments, which can interrupt continuous neuronal differentiation and neurite outgrowth of transplanted NSCs. To this end, biocompatible 3D bioscaffolds complexed with ECM proteins or peptides, such as laminin, fibronectin and Arginylglycylaspartic acid (RGD), that enhance neuronal differentiation of stem cells and neurite outgrowth continuously, have provided a promising solution for advanced stem cell-based tissue engineering. As such, inspired by a recent report on the non-covalent preparation of hydrogels, a method to generate biocompatible 3D-$MnO_2$ hybrid nanoscaffolds complexed with laminin-protein, termed, 3D-$MnO_2$-laminin hybrid nanoscaffolds was developed. Interestingly, $MnO_2$-laminin hybrid nanoscaffold, an innovative 3D-inorganic scaffold, that was self-assembled in laminin, was successfully synthesized by mixing 2D-$MnO_2$ nanosheets with laminin solutions (FIG. 3A). The self-assembly process could be achieved by the strong interactions of laminin toward 2D-$MnO_2$ nanosheets, where laminin can function as adhesive layers (binder) for individual 2-D $MnO_2$ nanosheets. To investigate whether 3D-$MnO_2$-laminin hybrid nanoscaffolds promote the neuronal differentiation of NSCs, and the associated neuronal behaviors, including neurite outgrowth, stem cell assays were performed using three different substrates/scaffolds (glass, $MnO_2$ nanoscaffolds, and 3D-$MnO_2$-laminin hybrid nanoscaffolds) under the same culture conditions. After 6 days of stem cell differentiation assays, dramatically higher cell counts were found from the 3D-$MnO_2$-laminin hybrid nanoscaffolds, compared to glass (740% higher) and $MnO_2$ nanoscaffolds (270% higher) controls (FIG. 3B). Furthermore, through a neuronal marker, beta-III tubulin (TuJ1) immunostaining, an even more significant improvement of neuronal differentiation and neurite outgrowth was observed from the 3D-$MnO_2$-laminin hybrid nanoscaffolds, compared to the other control substrates, showing 11 times longer average neurite lengths, compared to laminin-coated glass, and 1.7 times longer than laminin-coated $MnO_2$ nanoscaffold. Neurites from iPSC-NSCs differentiated on nanoscaffold and control scaffolds were first identified by tracing neurites using TuJ1 immunostained cells, then the lengths were recorded using Nikon NIS Elements software. The average neurite length was averaged from 10 measurements.

It was further verified that the neurons formed on the hybrid nanoscaffolds were functional through time-dependent calcium imaging techniques. The results clearly support the hypothesis that 3D-$MnO_2$-laminin hybrid nanoscaffolds can effectively, and steadily, promote neuronal differentiation of stem cells, and neuronal behaviors, for versatile stem cell therapies.

Example 5. Spatiotemporal Controlled Delivery of Soluble Cues Using 3D-Hybrid Inorganic Nanoscaffolds: Loading and Monitoring of Drug Release While some conventional biodegradable and biocompatible 3D-hybrid scaffolds have shown their potential to promote stem cell neuronal differentiation and neurite outgrowth, there is still a lot of room for improvement to control stem cell differentiation and neuronal behaviors in a more selective and temporally controlled manner in vivo. These requirements would be essential to achieve the full therapeutic potential of transplanted stem cells for SCI treatment. Addressing this challenge, spatiotemporal controlled delivery of soluble cues, such as small organic molecules (e.g. neurogenic drugs to selectively induce stem cell neuronal differentiation), using the 3D-hybrid inorganic nanoscaffolds of the present disclosure, provides a promising solution. Conventional scaffolds, that typically use physical encapsulation to load drugs, normally suffer from rapid diffusion of drugs, which leads to undesired damage to the transplanted cells, as well as the surrounding tissues, due to the high drug concentration initially, and limited neurogenic effect later on, due to an insufficient remaining drug concentration. To this end, the 3D-$MnO_2$-laminin hybrid nanoscaffolds of the present disclosure showed improved drug-loading capability and minimized burst-release, owing to strong drug-binding affinity to the nanoscaffolds. For a comprehensive study of drug loading and monitoring of drug release using the nanoscaffolds, a fluorescent aromatic ring-containing small molecule, Rhodamine B (RhB), was used as a model drug system. To optimize the loading and binding of drug molecules, RhB was first loaded onto 2D-$MnO_2$-nanosheets. Then, the RhB-loaded 2-D $MnO_2$-nanosheets self-assembled with laminin to generate 3D-$MnO_2$-laminin hybrid nanoscaffolds. A quantitative fluorescence resonance energy transfer (FRET)-based approach was used to monitor released or non-binding RhB molecules. The FRET-based method allowed for assaying the drug loading and release process. Based on this FRET-based drug monitoring method, an excellent drug-binding affinity onto the 3D-$MnO_2$-laminin hybrid nanoscaffolds was observed, wherein minimal RhB release from the nanoscaffolds was detected over 7 days. However, as soon as a bioreductant (vitamin C) was introduced to the RhB-loaded 3D-$MnO_2$-laminin hybrid nanoscaffolds, the fluorescence signal of RhB release was observed with an over 500-fold increase with a sustainable delivery profile (FIG. 5). This experimental result strongly indicated that the hybrid inorganic nanoscaffold-based drug delivery platform of the present disclosure can control drug release kinetics over a few weeks, through degradation of nanoscaffolds. On the other hand, the control polymer scaffolds burst-released over 20% of RhB, in the first 3 hours, under the same experimental conditions. Additionally, the stoichiometrically equivalent $Mn_{2+}$ ion release and the $MnO_2$ degradation (1:1 ratio) suggested that that MRI signals from $Mn_2^+$ can be utilized to quantify the degradation rate of the hybrid nanoscaffolds and to correlate the intensity of MRI signal with the amount of drug released. By inducing the nanoscaffold degradation by bioreductants, it was found that the amount of released drug, measured by the fluorescence intensity of RhB, was closely correlated with the intensity of the MRI signal. This "on/off" MRI-based monitoring of drug release has not yet been demonstrated in conventional scaffolds, thereby offering a new tool that can provide a much-improved investigation on drug delivery and in vivo release.

The optimized condition regarding drug loading and release, based upon the fluorescent RhB molecule as a model drug, was used to load and deliver neurogenic drugs for an enhanced neuronal differentiation. To screen the optimal neurogenic drug, the aforementioned DFT calculations (Table 1) were applied, and a neurogenic drug (DAPT) was selected based upon its high binding energy to 2D-$MnO_2$ nanosheet. DAPT is a γ-secretase and Notch inhibitor that simultaneously promotes neuronal differentiation and neurite outgrowth, while suppressing astrocyte differentiation. The calculated binding energy between DAPT and the 2D-$MnO_2$ nanosheet was-18.3 kcal/mol, an over 4-fold increase, compared to the binding of solvent (water) to nanoscaffolds, indicating that DAPT drugs can be strongly adsorbed to the $MnO_2$ surface. The binding energy was calculated by the equation of E (BE)=E(A+B)−E(A)−E(B), and was summarized in the unit of kCal/mol. Indeed, by forming DAPT-loaded 3D-$MnO_2$-laminin hybrid nanoscaffolds, the spectrums from matrix-assisted laser desorption/ionization (MALDI) time-of-flight (TOF) mass spectrometer showed a high amount of DAPT loaded onto the nanoscaffolds, while control scaffolds (glass and polymer substrate) did not show any noticeable peaks. To investigate the effect of DAPT-loaded 3D-MnO$_2$-laminin hybrid nanoscaffolds on stem cell neuronal differentiation and neuronal behaviors, hiPSC-NSC-based neuronal differentiation assays were tested using DAPT-loaded 3D-MnO$_2$-laminin nanoscaffolds, and related controlled conditions for one week. A strong enhancement of neuronal differentiation was found from the DAPT-loaded 3D-MnO$_2$-laminin nanoscaffold condition (1.4-fold enhancement of Tuj 1 mRNAs compared to 3D-MnO$_2$-laminin hybrid nanoscaffolds, 1.7-fold enhancement of neurite outgrowth), as well as suppressed GFAP mRNA expression. Remarkably, in the boundary of DAPT-loaded 3D-MnO$_2$-laminin hybrid nanoscaffold and glass, NSC-derived neurons across the boundary, cultured under the same conditions, had a dramatic change in morphology and neurite outgrowth. This result provides a direct comparison between the 3D-MnO$_2$-laminin hybrid nanoscaffolds of the present disclosure and conventional scaffolds, and indicates the ability of spatiotemporal control of hiPSC-NSC differentiation using the drug-loaded 3D-hybrid inorganic nanoscaffolds systems.

Example 6. Advanced Stem Cell Therapy for Enhanced Treatment of Spinal Cord Injury (SCI)

With the prominent effects of the 3D-hybrid inorganic nanoscaffolds on improving the adhesion, neuronal differentiation of hiPSC-NSCs, and neurite outgrowth of differentiated neurons, the therapeutic effect of the nanoscaffold-supported hiPSC-NSC transplantation for enhanced SCI treatment was tested (FIG. 4A). To transplant the stem cell seeded-nanoscaffolds into the SCI lesion, a T10 thoracic hemisection lesion to the spinal cord of an adult mouse was generated, then the hiPSC-NSC seeded-nanoscaffolds, as an experimental condition, and -polycaprolactone (PCL) polymer scaffolds, as a control condition, were rolled up and inserted into the hemisected SCI lesion (FIG. 4A). Surgifoam inserted mice were used as a sham control condition. After transplantation, nanoscaffold biodegradation was evaluated in vivo by detecting the amount of degraded Mn (manganese) element in mouse urine samples using inductively coupled plasma mass spectrometry (ICP-MS) analysis. Among the 6 common elements (Ca, Zn, Na, Fe, Mn, Mg) detected in the urine, only Mn level was significantly increased in nanoscaffold, compared to the polymer control in the elemental analysis, was attributed to the degradation of MnO$_2$ transplanted in the spinal cord region. Consistent with previous in vitro studies, rapid in vivo degradation of nanoscaffold was observed. This degradation of transplanted nanoscaffolds was also detected by the color change (from black to brown), in a time-dependent manner, throughout the first-week, post-transplantation. Even though the timely-biodegradability of transplanted scaffolds would be required to better control drug release spatiotemporally, and to facilitate the integration of transplanted stem cells into the injured areas, it has not been well achieved in conventional polymer scaffolds for SCI treatment. More importantly, to quantitatively compare the nanoscaffold-based therapeutic effect on the functional recovery of SCI mice to the two different control conditions, the well-established Basso Mouse Scale (BMS) for the evaluation of behaviors post-injury was used (FIG. 4C). In the first 7-days post-transplantation, as expected, no mice, among three different conditions, showed any motor function recovery (BMS scores: 0; full scale: 9). After 2 weeks of transplantation, most of the SCI mice treated with stem cell seeded-nanoscaffolds and PCL-polymer scaffold started showing promising recovery of a plantar placing (BMS scores: 3), while the sham group mostly stayed in the stage of ankle movement (BMS scores: 2.5). The enhanced functional recovery from the stem cell-seeded nanoscaffold group, compared to the PCL-polymer group and sham group, became much more obvious 3-weeks post-injury, where SCI mice from the nanoscaffold group scored 6, based on BMS, while SCI mice from the PCL-polymer group and sham group averaged 4.5 and 3.5, respectively. This significantly enhanced therapeutic effect from the nanoscaffold condition continued throughout the whole 7-week analysis period, and the SCI mice treated by stem cell seeded-nanoscaffold obtained the highest functional recovery, with frequent or consistent plantar stepping at Week 7 (BMS score: 5), whereas mice from the PCL-polymer group and sham group stabilized at BMS score of 3 (plantar placing) and 2 (ankle movement), respectively. Even though the detailed underlying mechanisms of stem cell transplantation-promoted SCI functional recovery have not been well understood, without wishing to be bound by theory, many scientists believe that scaffold-based approaches can enhance the survival and differentiation of stem cells, which results in reduced glial scar formation and reestablished neural circuits (FIG. 4B).

To better understand molecular and cellular mechanisms of the nanoscaffold-enhanced functional recovery, compared to the two control groups, the adhesion, proliferation, and neuronal differentiation of the transplanted hiPSC-NSCs in the first-week post-transplantation, was examined using immunohistological staining. While no obvious change in inflammatory markers between these 3 groups of mice was observed both 7-day and 7-week post-injury, the nuclei staining results showed that the nanoscaffold strongly improved adhesion and survival of hiPSC-NSCs in vivo, as indicated by the dramatically higher number of hiPSC-NSCs remaining on the transplanted sites, compared to the PCL-polymer scaffold. Cells stained with DAPI, but not expressing GFP fluorescence, were considered as transplanted cells. Almost all of these cells were densely adhered on the surface of MnO$_2$ laminin hybrid nanoscaffold. In contrast, staining images from the SCI site transplanted with iPSC-NSCs seeded PCL scaffold did not show successful transplantation of cells, as indicated by an absence of anti-human staining markers, and significantly reduced nuclei staining found surrounding the PCL scaffold. Moreover, significantly higher populations of proliferation marker phosphohistone H3 (PH3) were observed from the nanoscaffold condition, compared to the control conditions. Furthermore, an increased expression of TuJ1 (neuronal marker) was observed during the first week of transplantation, whereas no noticeable neuronal markers were observed on hiPSC-NSCs surrounded PCL scaffolds, suggesting the nanoscaffolds can promote hiPSC-NSC differentiation into neurons in vivo. It was additionally found that a majority of TuJ1 positive cells differentiated on the nanoscaffold were co-labelled with MAP2 and Synapsin 1. It was found that a majority of TuJ1 positive cells differentiated on the nanoscaffold were co-labelled with MAP2 and Synapsin 1. MAP2 protein belongs to the microtubule-associated protein family that are enriched in dendrites; Synapsin is a neuronal marker associated with functional matureation of neuronal synapses. Both proteins are well known markers for characterizing mature neurons. Most importantly, the nanoscaffold group showed obviously less glial scar formation from the GFAP (astrocyte marker) immunohistological staining of tissue slices 7-week post-transplantation, whereas both controls showed distinctly more intensive glial scar formation from GFAP immunohistological staining data. This suggests a long-term survival, and successful differentiation of iPSC-NSCs transplanted by the nanoscaffold of the invention. In comparison, minimum cells and neuronal markers were found surrounding PCL scaffolds at week 1. These results were further supported with reduced cavities and more continuous neuronal networks 7-week post-injury existent in the nanoscaffold treated group, comparing to the PCL-polymer scaffold group, which could be direct indications of enhanced recovery from injury. While the detailed mechanisms behind the nanoscaffold-based enhancement of functional recovery still require further investigation, the successfully improved hiPSC-NSC transplantation, enhanced neuronal differentiation in vivo, and functional recovery in mouse SCI model, strongly suggest great potential of nanoscaffold-based stem cell therapy as a novel treatment for SCI and for advancing neural tissue engineering.

Example 7. Additional Modulation of Nanoscaffolds

The nanoscaffolds were modified including i) varying thickness, which was achieved through adjusting the amount of nanosheets deposited and ii) interlayer binding species (ions and proteins). Both showed reliable control over full degradation time under identical redox conditions. Briefly, the increased thickness of nanoscaffold directly slowed down the degradation. Larger interlayer binding molecules (e.g. bovine serum protein or laminin) introduced during the self-assembly led to faster degradation, as compared to ion species existent inside scaffolds. Control over degradation in the absence of additional bioreductants was additionally demonstrated, by simply varying the cell densities transplanted on the nanoscaffold. Specifically, when no cells were transplanted, the scaffold was found to be stable for over a month, without any noticeable degradation. In contrast, with cell transplantation, degradation occurred in a cell density dependent manner. These results collectively support the ability to control degradation speed of the $MnO_2$ nanoscaffold, other than by modulating in vivo redox microenvironments. Redox conditions (ascorbic acid concentration of 10 μg/mL) were kept constant and physiologically relevant for all of the conditions. The degradation profile was precisely monitored by measuring time-dependent concentrations of manganese elements that dissolved in the solution through ICP-MS. The percentage of degradation at each individual time point was normalized to total amount of manganese existent in the nanoscaffolds prepared. The results are summarized in FIG. 6. All degradation profiles showed zero-order degradation kinetics for most of the time, clearly demonstrating the wide range tunability of scaffold biodegradation by comparing different profiles. Briefly, reducing the thickness of nanoscaffold by 5 times was shown to increase the degradation speed by about 3 times; increasing the aspect ratio, while maintaining 2-D $MnO_2$ nanosheets the same, slowed down the degradation speed by over 10 times; and increasing the protein concentrations utilized to assemble the nanosheets lead to a significant degradation speed increase of around 7 times. Overall, the degradation of $MnO_2$ nanoscaffold can be controlled from full degradation by 3 days, to less than 30% degradation after 3 weeks, which covers the wide range desirable under different tissue engineering applications.

In addition to tuning the scaffold structure, scaffold degradation was modulated in the absence of any exogenous trigger, such as ascorbic acid. To this end, different amounts of iPSC-NSCs (N=0, 0.5, 1.0 and 5.0 million) were transplanted to achieve such controllable degradation. iPSC-NSC differentiation media, without any additional bioreductants, was used for this Example, and the full degradation of scaffold was monitored based on the complete disappearance of brown colored 2-D $MnO_2$ nanosheets. When no cells were seeded onto the scaffold, no noticeable degradation from the $MnO_2$ nanoscaffold happened throughout one-month period of observation. With cell transplantation, the degradation time showed a clear cell density-dependent trend. Briefly, transplanting 5 million iPSC-NSCs lead to scaffold degradation within 2 days, while 0.5 million cells led to scaffold degradation over 2 weeks. As such, it was concluded that scaffold degradation can be readily controlled.

The foregoing examples and description of the preferred embodiments should be taken as illustrating, rather than as limiting the present invention as defined by the claims. As will be readily appreciated, numerous variations and combinations of the features set forth above can be utilized without departing from the present invention, as set forth in the claims. Such variations are not regarded as a departure from the scope of the invention, and all such variations are intended to be included within the scope of the following claims. All references cited herein are incorporated by reference in their entireties.

The invention claimed is:

1. A biodegradable scaffolding material comprising a hybrid support structure consisting of manganese dioxide support structures, and at least one of a plurality of extracellular matrix proteins or a plurality of extracellular matrix polysaccharides,
   wherein the manganese dioxide support structures consist of two-dimension nanosheets;
   wherein the manganese dioxide support structures define a structure comprising a plurality of interstices and the plurality of extracellular matrix proteins or plurality of extracellular matrix polysaccharides are disposed around and between the manganese dioxide support structures and through the manganese dioxide support structure interstices;
   wherein the extracellular matrix proteins or extracellular matrix polysaccharides have a binding affinity with the manganese dioxide support structures, and together form at least one 3-dimensional nanoscaffold, and
   wherein either the nanoscaffold thickness, protein concentrations utilized to assemble the two-dimension nanosheets, or both, are selected in combination with the aspect ratio of the nanoscaffold to set the zero-order degradation rate of the nanoscaffold.

2. The biodegradable scaffolding material of claim 1, wherein the extracellular matrix proteins comprise at least one of collagen, elastin, laminin, fibronectin, gelatin, a reconstituted basement membrane extracted from Engelbreth-Holm-Swarm mouse tumor, entactin, proteoglycans, or basement membrane protein.

3. The biodegradable scaffolding material of claim 2, wherein the extracellular matrix proteins comprise laminin.

4. The biodegradable scaffolding material of claim 1, wherein the extracellular matrix polysaccharides comprise at least one of hyaluronic acid, alginate, chitosan, or combinations thereof.

5. The biodegradable scaffolding material of claim 1, further comprising at least one cell that is loaded onto the manganese dioxide support structures.

6. The biodegradable scaffolding material of claim 5, wherein the at least one cell comprises stem cells.

7. The biodegradable scaffolding material of claim 6, wherein the stem cells comprise neural stem cells.

8. The biodegradable scaffolding material of claim 1, further comprising at least one therapeutic agent that is loaded onto the manganese dioxide support structures.

9. The biodegradable scaffolding material of claim 8, wherein the therapeutic agent comprises at least one of a protein, antibody, nucleic acid, biologic drug, peptide, small molecule, ligand, cytokine, chemotherapeutic agent, antipyretic, analgesic, anesthetic, antibiotic, antiseptic, hormone, stimulant, depressant, statin, beta blocker, anticoagulant, antiviral, anti-fungal, anti-inflammatory, growth factor, vaccine, diagnostic composition, psychiatric medication, or psychoactive compound.

* * * * *